(12) United States Patent
Chun

(10) Patent No.: US 10,517,915 B2
(45) Date of Patent: Dec. 31, 2019

(54) METHOD FOR PREPARING GARLIC-FERMENTED COMPOSITION AND GARLIC-FERMENTED COMPOSITION PREPARED BY SAME METHOD

(71) Applicant: Hyun Soo Chun, Seoul (KR)

(72) Inventor: Hyun Soo Chun, Seoul (KR)

( * ) Notice: Subject to any disclaimer, the term of this patent is extended or adjusted under 35 U.S.C. 154(b) by 313 days.

(21) Appl. No.: 15/306,090

(22) PCT Filed: Apr. 22, 2015

(86) PCT No.: PCT/KR2015/004028
§ 371 (c)(1),
(2) Date: Oct. 22, 2016

(87) PCT Pub. No.: WO2015/163694
PCT Pub. Date: Oct. 29, 2015

(65) Prior Publication Data
US 2017/0119839 A1    May 4, 2017

(30) Foreign Application Priority Data

Apr. 22, 2014  (KR) ........................ 10-2014-0048259

(51) Int. Cl.
| | |
|---|---|
| *A61K 36/8962* | (2006.01) |
| *C12P 1/04* | (2006.01) |
| *A23L 19/00* | (2016.01) |
| *A23L 27/10* | (2016.01) |
| *A23L 33/105* | (2016.01) |
| *A23L 27/24* | (2016.01) |
| *C12R 1/125* | (2006.01) |

(52) U.S. Cl.
CPC .......... *A61K 36/8962* (2013.01); *A23L 19/00* (2016.08); *A23L 27/10* (2016.08); *A23L 27/105* (2016.08); *A23L 27/24* (2016.08); *A23L 33/105* (2016.08); *C12P 1/04* (2013.01); *A23V 2002/00* (2013.01); *A61K 2236/00* (2013.01); *C12R 1/125* (2013.01)

(58) Field of Classification Search
None
See application file for complete search history.

(56) References Cited

U.S. PATENT DOCUMENTS

| | | | | |
|---|---|---|---|---|
| 2009/0208470 | A1* | 8/2009 | Park ...................... | A01N 63/04 424/93.51 |
| 2009/0285920 | A1* | 11/2009 | Lee ........................ | A01N 63/02 424/754 |
| 2011/0129580 | A1* | 6/2011 | Ko ......................... | A23B 7/005 426/419 |

FOREIGN PATENT DOCUMENTS

| | | |
|---|---|---|
| KR | 10-2008-0026356 A | 3/2008 |
| KR | 10-2008-0046830 A | 5/2008 |
| KR | 10-2008-0082945 A | 9/2008 |
| KR | 10-1037101 * | 5/2011 |
| KR | 10-1086270 B1 | 11/2011 |
| KR | 10-2013-0143410 * | 12/2013 |
| KR | 101346139 B1 | 12/2013 |

* cited by examiner

*Primary Examiner* — Susan Hoffman
(74) *Attorney, Agent, or Firm* — Maschoff Brennan

(57) ABSTRACT

The present invention relates to a method for preparing a garlic-fermented composition and a garlic-fermented composition prepared by the method, and the purpose of the present invention is to provide a garlic-fermented composition which is easy to take, has no side effect, and improves excellent pharmacological and physiological efficacies of garlic. To achieve this, the method for preparing a garlic-fermented composition according to an aspect of the present invention, comprises: a first fermentation step of mixing garlic, water, and a ferment strain, followed by fermentation, thereby decomposing and converting sugars and proteins of the garlic; and a second fermentation step of additionally supplying a carbon source to a filtrate obtained through solid-liquid separation of the fermented product, followed by fermentation, thereby removing ammonia of the filtrate and decomposing and converting the additionally supplied carbon source.

5 Claims, 22 Drawing Sheets

Normal control     $FeCl_3$ thrombosis-caused experimental control     $FeCl_3$ thrombosis-caused - garlic-administrated control

Figure 17a (Unit: mmHg)

| No. | Classification | Rat before drinking | 15 minutes after drinking | Remarks |
|---|---|---|---|---|
| 1 | Sex: male/age: early 50s/job: business<br>Symptom: borderline blood pressure for 10 years (in the use of a hypertension medicine) | 145-95 | 123-82 | - |
| 2 | Sex: female/age: 50s/job: housewife<br>Symptom: in the use of a hypertension medicine for 10 years | 180-103 | 138-87 | 130 even after the use of a hypertension medicine. |
| 3 | Sex: male/age: later 50s/job: politician<br>Symptom: he took a cardiovascular operation, and blood pressure does not drop even though a hypertension medicine is taken | 170-109 | 143-95 | Condition is getting better. |
| 4 | Sex: male/age: early 60s/job: business<br>Symptom: doctor suggests the use of a hypertension medicine (he does not take a hypertension medicine) | 148-90 | 30minutes 128-77 | |
| 5 | Sex: male/age: 40/job: employee<br>Symptom: in the use of hypertension medicine | 148-94 | 30minutes 135-82 | - |
| 6 | Sex: male/age: middle 50s/job: business<br>Symptom: weight is gaining and a hypertension value is rising in recent years, stiffness in the back neck (not in the use of any hospital medicine. | 150-98 | 120-80 | He feels light and has the feeling of cleaned eyes. |
| 7 | Sex: male/age: middle 50s/job: business<br>Symptom: fell 3 years ago (in the use of a hypertension medicine. | 146-95 | 125-80 | |
| 8 | Sex: female/age: 50 / female<br>Symptom: hypertension and headache | 163-92 | 128-82 | Headache and diarrhea are gone. |
| 9 | Sex: male/age: late 40s/job: business<br>Symptom: currently doing an exercise due to the weight gaining for a short period, and 150~95 of blood pressure | 162-92 | 116-75 | He feels light. |
| | It is confirmed that the average blood pressure was dropped 20~30% and this state was maintained for more than 3 hours. | | | |

METHOD FOR PREPARING GARLIC-FERMENTED COMPOSITION AND GARLIC-FERMENTED COMPOSITION PREPARED BY SAME METHOD

TECHNICAL FIELD

The present invention relates to a method for preparing a garlic-fermented composition and a garlic-fermented composition prepared by same method which is able to facilitate an easier intake without causing any side effect and may provide enhanced pharmacological and physiological efficacies of garlics.

BACKGROUND ART

As a human's lifespan increases, a lifestyle-related disease (a chronic disease), for example, a cardiovascular disease, a cancer, diabetes mellitus, obesity, dementia, etc. increasingly follows. For this reason, a demand for taking a health strengthening food increases, which is able to maintain and improve a physiological function.

The cardiovascular disease related with a blood circulation disorder may cause an artery hardening, a stroke, etc. which is considered a key death cause throughout the world. According to a report from the Korea Institute for Health and Social Affairs, such diseases are related to the highest death rate following the cancer.

The normal blood circulation is very accurately adjusted by a nervous system and various hormones. The reason why a blood circulation-related disease increases in diversified modern societies is related with multi-causes, for example, a genic factor, the intake of a high fat food, a high protein food, deviated lifestyles, a contaminated life environment and society, an economic stress, etc.

The technology in a BT (Bio Technology) field for a prolonged human's lifespan and an improved health is mainly related with the development of a new bioactive substance using a natural thing and the development of a product using the same. In particular, a garlic is a representative spice and a food material which is gaining interests since the disclosure of a report saying that the garlic provides various bioactive ingredients, for example, an anti-cancer function, an anti-inflammatory function, etc.

The garlic (*Allium sativum* L.) is a perennial root plant and belongs to a lily and *allium* genus and is one of representative cultivation plants which have been cultivated for more than 5-thousand years. It is reported that the garlic has an effect to increasing the level of immunity, an effect to increasing a resistance with respect to a pathogenic bacteria and a cancer cell, an effect to preventing and curing a circulatory organ disease (refer to Table 1).

TABLE 1

|  |  |  | Minerals |  | Vitamins |  |  |  |  |  |
|---|---|---|---|---|---|---|---|---|---|---|
|  |  |  |  |  |  |  |  | Nacin |  |  |
| Energy (kcal) | Protein (g) | Fat (g) | Ca (mg) | Fe (mg) | A (IU) | B1 (mg) | B2 (mg) | Equivalent (mg) | C (mg) | Waste ratio |
| 145 | 3.0 | 0.5 | 32 | 1.6 | — | 0.33 | 0.52 | 0.1 | 7 | 10 |

| Components | Representative efficacies | Main efficacies |
|---|---|---|
| Zinc | Stamina strengthening, Robustness strengthening | It acts in a human body and strengthen strength, and increase vitality of human body's organ and cell<br>It expands peripheral blood vessels and promotes a blood circulation.<br>It improves a menopause disorder and reinforces a stamina for a middle age person. |
| Germanium Selenium | Blood circulation improvement, hypertension, artery hardening (myocardial infraction, angina pectoris, stroke) | Detoxification, sterilization: it eliminates a cholesterol in blood.<br>It acts to adjust a blood pressure.<br>It provided an anticancer effect. |
| Allicin | Detoxification, sterilization | It discharge a heavy metal in a human body and detoxifies a harmful substance, and helps an evacuation.<br>It provides a strong sterilizing power and an immunity adjusting function. |

The unique flavor of a food may be lost or changed due to heat, light, air, pressure, etc., and the scent thereof may be eliminated due to heat. The allicin which is a component of the flavor and hot taste may be eliminated at over 70° C. In this regard, various ways, for example, a crushing way, a roasting way, etc. are developed and used. The aforementioned heating method may be advantageous in the way that a product can be manufactured for a short time period, and a sterilization effect is good due to heat treatment; however the components, for example, vitamins, various minerals, and various amino acids of the garlic may be destroyed, which may cause a lot of loss of useful components of the garlic. In particular, a flavonoid component which is known as having a useful effect, may be destroyed, and enzyme may be eliminated. For the sake of a long time distribution of the product, the use of a predetermined preserved agent is inevitable.

DISCLOSURE OF INVENTION

The inventor of the present invention has researched in many ways to eliminate a garlic smell and hot taste, which have been a problem when eating, while promoting good pharmacological and physiological efficacies. As a result of such researches, the inventor has recognized that if the garlic is processed by a non-heating method using a fermentation strain, functional components increase, and a hot taste can be eliminated, and the garlic becomes good to a health, which makes it possible to easily eat without any sense of repulsion. If the garlic is overly eaten, there is not any side effect. The inventor has completed his invention in this way.

Accordingly, it is an object of the present invention to provide a method for preparing a garlic-fermented composition and a garlic-fermented composition prepared by same method, which mat allow to prepare a garlic-fermented composition which is able to provide enhanced pharmacological and physiological efficacies without any side effect, thus contributing to promoting the health of a modern man.

To achieve the above objects, there is provided a method for preparing a garlic fermented composition, which may include, but is not limited to, a first fermentation step wherein a garlic, water and a fermentation strain are mixed and fermented, thus decomposing and transforming the sugar and protein of the garlic; and a second fermentation step wherein a fermentation is carried out in such a way to add a carbon source to a filtrate obtained by separating the fermented mixture into a solid and a liquid, thus eliminating ammonia of the filtrate, and the additionally supplied carbon source is decomposed and transformed.

Here, the amount of the water is 1~20 times of the garlic with respect to the parts by weight, and the amount of the fermentation strain is 0.01~1 parts by weight with respect to 100 part by weight of the mixture of the garlic and the water.

Moreover, in the first fermentation step, a monosaccharide or a disaccharide and the fermentation strain are added to the water, and an activation of the fermentation strain is first guided, and then the garlic is added, and the fermentation is carried out.

In addition, the first fermentation step is carried out for 3 to 15 days at 20~40° C.

Furthermore, the fermentation strain is a *Bacillus subtilis* subsp. *subtilis* (Microorganism deposit number KACC91554P).

Moreover, the carbon source is one or more than one mixture selected from a group consisting of fruits, for example, a persimmon skin, a kiwi, a pineapple, a pear, a grape, berries, etc. and an onion, a honey, etc.

In addition, in the second fermentation step, the amount of the supply of the carbon source added in the second fermentation step is calculated after the content of the organic substance and ammonia of the filtrate has been quantitatively measured and is referred to the lacking amount of the amount of the organic substance necessary to eliminate the ammonia.

Furthermore, the second fermentation step is carried out for 1 to 7 days at 20~40° C. until the sugar level of the filtrate becomes below 0.3 brix.

Moreover, the preparation method further includes an ultrafiltration step for eliminating a fermentation strain and a residue of the fermented substance after the second fermentation step, and a disinfection step or a sterilization step after the second fermentation step.

In addition, there is provided a garlic fermented composition prepared by the preparing method.

Furthermore, there are provided a pharmaceutical composition containing as an effective component a garlic fermented composition prepared by the preparing method, and a health function food containing as an effective component a garlic fermented composition prepared by the method of any one of claims 1 to 10.

Advantageous Effects of the Invention

The garlic fermented composition according to the present invention may allow to provides the following effects: a blood flow improvement, a blood flow rate improvement, a thrombus creation reduction, an inhibition of a collagenous fiber damage in a blood vessel, a body fat loss, a lowered blood pressure, a reduced total cholesterol, a reduced liver cell damage, etc.

Moreover, the present invention may provide the effects, for example, a hypertension prevention, a brain disease, diabetes mellitus, hyperlipidemia and liver function improvements, a heart disease prevention, an enhanced anti-oxidative activity, etc. Moreover, there are effects, for example, a lost body weight, a deep sleep, a detox function for discharging a body inflammation, and improvements in various neuralgia, chronic sinusitis, chronic rhinitis, etc.

In particular, the garlic fermented composition according to the present invention may allow to improve a fat liver and hypertension due to an obesity, and to increase the number of reduced sperms.

Moreover, the garlic fermented composition according to the present invention may allow for a reduced loss of an effective component of the garlic since it is processed by the non-heating method, and the composition is made in the form of a nano-molecular which may facilitate a digestion absorption, and a long time distribution of the product is available without using any preserved agent.

In addition, the garlic fermented composition according to the present invention may provide a quick absorption and an instant effect. For example, the blood pressure may drop 10~30% in 20 minutes after the drinking, and as a result of the heart pulse wave measurement, the blood vessel health index becomes 20% better in 5~10 minutes, and the body temperature of a cold body patient increases over 2° C. in average. The aforementioned effects have never been reported in a conventional health-related product and medicine.

Furthermore, the garlic fermented composition according to the present invention is easy to drink or eat since it does not have any garlic smell and hot taste, and it can be widely used to manufacture a health-related functional food by adding to various foods, so the applicable range thereof can be increased, and a high value-added product can be manufactured.

Moreover, the garlic fermented composition according to the present invention has a good effect in a circulatory organ disease including a heart blood vessel. Since it does not cause any side effect, the present invention may contribute a lot to a people's health enhancement and an economic benefit related with a medical expenses.

BRIEF DESCRIPTION OF DRAWINGS

FIG. 17A is a table showing a result of a clinical experiment of a garlic fermented composition according to the present invention, which was carried out with respect to a hypertension patient.

BEST MODES FOR CARRYING OUT THE INVENTION

Figure 1:
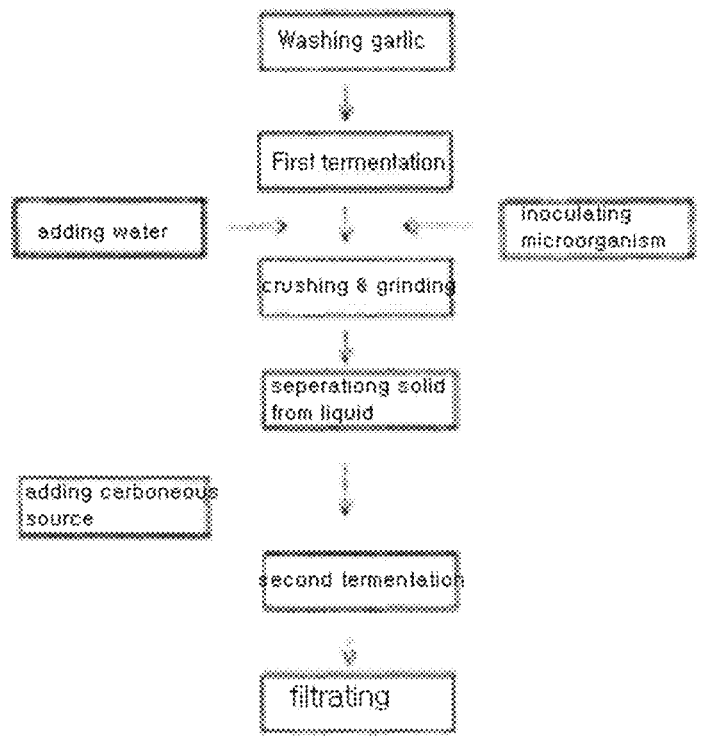
FIG. 1 is a block diagram illustrating a method for preparing a garlic fermented composition according to a preferred embodiment of the present invention.

The method for preparing a garlic fermented composition according to the present invention will be described with reference to FIG. 1.

(1) Preparation of Main Ingredients

① Garlic

The garlic can be used as an ingredient after a refresh garlic is peeled and washer and crushed or it is steamed.

② Fermentation Strain

Any kinds of fermentation strains may be available as long as it is able to ferment a garlic. In the present invention, a *Bacillus subtilis* subsp. *subtilis* (Microorganism deposit number KACC91554P) was used.

(2) First Fermentation

This was referred to a process wherein the crushed refresh garlic or the steamed garlic and water and a fermentation strain are were mixed and aerobically fermented, and the sugar and protein of the garlic were decomposed.

The natural product formed of a single substance may have both a medicine property and a toxic property. There may be a limit to eliminating the toxic component and extracting the medicine component when preparing a health-related food and medicine. The fermentation is referred to a process wherein the toxic component is eliminated while increasing and doubling the medicine component. The present invention is intended to eliminate the toxic component of the garlic through the fermentation while increasing the medicine component.

It is preferred that the amount of water is 1~20 times of the garlic in terms of their weight, and the amount of the fermentation strain is 0.01~1 part by weight with respect to 100 parts by weight of the mixture of the garlic and water.

For the sake of an efficient fermentation, 0.5~1.5% of a monosaccharide or a disaccharide the amount of which was appropriate for the cultivation of the microorganism and a corresponding amount of the fermentation strain were added to a corresponding amount of water, and it was cultivated for a predetermined time, and the maximum activation of the microorganism was guided first, and then a corresponding garlic was inputted, and the mixture was fermented.

The dissolved oxygen (DO) concentration based on the ratio of the sugar and protein of the garlic was set, and the air was injected using a small foaming device which was installed separate, and the appropriate temperature based on the optimum fermentation was controlled.

The mixture of the garlic, water and fermentation strain was fermented for 3~15 days at 20~40° C., during which the protein would be decomposed, so the amino nitrogen content, the protease activity and the number of living bacterium were shown high.

(3) Second Fermentation

This was referred to a process wherein the fermented substance was subjected to a solid-liquid separation, and a filtrate was obtained, and a carbon source was added to the filtrate which was lack of carbon, and the ammonia of the filtrate was removed, and the added carbon source was decomposed.

During the fermentation procedure, the amino acid was decomposed, during which the ammonia was produced. It is advantageous that the growth of other bacterium can be inhibited thanks to the presence of the ammonia, but a bad smell occurred due to decay. The ammonia was the index which showed a food decay or an abnormal fermentation.

In order to eliminate the ammonia according to the present invention, the contents of the organic substance of the filtrate and the ammonia were quantitatively measured, and the organic substance which was necessary to eliminate the ammonia was calculated, and the lacking carbon source was added, and then the fermentation was carried out.

The concentration measurement of an accurate organic substance is an important measurement index in terms of a complete fermentation. There is not any fermentation example which has been carried out by applying a garlic or other high concentration substances to the food through any of the CODMn method and the CODcr method.

In the present invention, the concentration of the organic substance was measure using the CODcr method. The CODMn method which is mainly used as a concentration measurement method of an organic substance is not able to measure after recognizing an organic substance which can be decomposed by microorganism and an organic substance which cannot be decomposed thereby, for which the accuracy may become very low at a high concentration. Compared to the aforementioned method, the CODcr method is able to measure after it recognizes an organic substance that a microorganism is able to decompose and an organic substance that a microorganism is not able to decompose, for which the accurate is high at a high concentration.

If the lacking carbon source is supplied with respect to the content of the organic substance the microorganism is able to decompose, a complete fermentation may be carried out.

It is preferred that the product of the carbon source which is able to maximize the medicine property for each disease symptom, is added. For example, the carbon source having a medicine property may be any of the fruits, for example, a persimmon skin, a kiwi, a pineapple, a pear, a grape, a berry, etc. and an onion and a honey. The flavonoid component or other nutrition component are able to enhance the medicine property of the garlic and are able to provide a soft taste while extending a staying time in a body.

The filtrate to which the carbon source is added, is fermented under the optimum fermentation condition. The fermentation condition can be established optimum after considering the number of living bacterium of the filtrate and the characteristic of the fermentation strain. The fermentation period is referred to a period until the blood sugar becomes below 0.3 brix after the blood sugar of the filtrate is measured. The average fermentation temperature is 20~40° C., and the fermentation period is about 1~7 days.

The method for extracting a useful component using an organic solvent may obtain both a medicine property and a toxic component of the natural product; however the fermentation process which uses a microorganism, is able to decompose toxic components while maximizing a medicine property, and it is able to increase an absorption ratio, and since the organic solvent is not used, it is advantageous that a recovery cost is low.

The extraction process has a low recovery ratio of the useful component, and the first and second fermentations of the present invention may provide over 90% of the recovery ratio of the useful component, whereby it is possible to recover the useful components with a high concentration.

Moreover, the useful components may be changed into a nano-molecular by means of the microorganism, which may increase the absorption ratio, and since the useful components can be changed into an enzyme, the enzyme in the body is not used, and instead it can be advantageously converted into a metabolism energy. Most of the enzyme may be eliminated by a junk food, an aging process, etc. and the depletion of the enzyme may cause an aging and a disease. The fermented food made using a microorganism may be used as a metabolism energy without separating using the enzyme in our body.

(4) Ultrafiltration

This was referred to a process wherein the fermentation strain and residue in the fermented substance were removed through the ultrafiltration of the fermentation liquid which had been subjected to the second fermentation. The garlic fermented composition liquid of the present invention was prepared through the aforementioned procedures. The thusly prepared products can be stored for a long time if a preserved agent of the food is not added.

Instead of using the ultrafiltration method, the product may be prepared in such a way that the fermentation substance is processed by a common disinfection method or a sterilization method.

The present invention will be described in details through the embodiments. It is obvious to a person having ordinary kill in the art that the following embodiments are provided for illustrative purposes, not limiting the light scope of the present invention. The simple modification or changes of the present invention may be available by a person having ordinary skill in the art, and these modification or changes may belong to the region of the present invention.

Embodiments

A filtrate was prepared in such a way that 100 g of sugar was added to 10 kg of water at 25° C., and 2 g of *Bacillus subtilis* subsp. *subtilis* (Microorganism deposit number KACC91554P) was added and cultivated for 5 hours at 25° C., and 1 kg of the crushed refresh garlic was added, and was aerobically fermented for 10 days, and a solid and liquid were separated. 50 G of a persimmon skin crushed with a natural carbon source added to eliminate the ammonia was added and second fermented for 5 days at 25° C.

It was confirmed that the sugar content of the concentration fermentation liquid was below 0.3 brix, and the fermentation liquid was filtered using a typical ultrafiltration filter, thus finishing a garlic fermented composition liquid according to the present invention.

<Experiment 1: Animal Experiment> Verification on Blood Flow Circulation Effect

The rats were divided into 1) a normal diet experimental control, 2) a high fat diet experimental control and 3) a high fat diet control wherein 200 mg/kg of the garlic fermented liquid of the present invention was fed according to the embodiments, and the rats were raised for 12 weeks, and the efficacies of the product of the present invention were surveyed.

1-1. Blood Circulation Improvement Effects

Figure 2:
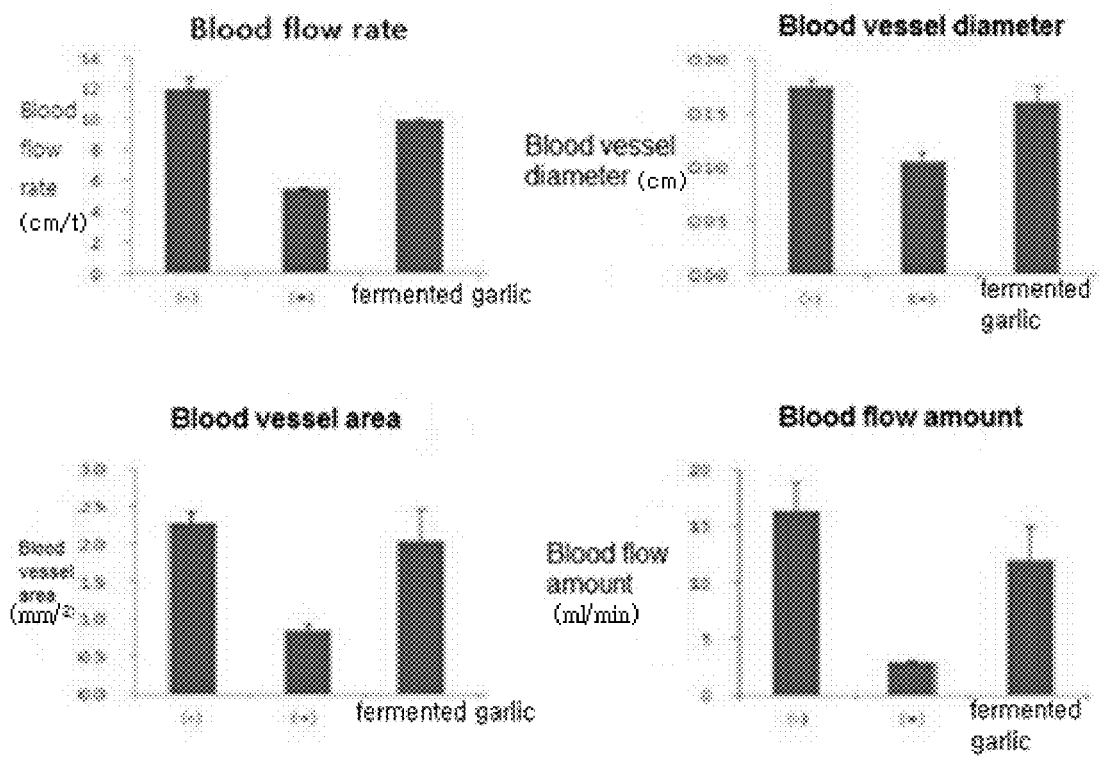
FIG. 2 is a comparison graph showing a blood flow rate, a blood vessel diameter, a blood vessel area and a blood flow amount of an experiment rat so as to show a flood flow improvement effect of a garlic fermented composition according to the present invention.

FIG. 2 is a comparison graph showing a blood flow rate, a blood vessel diameter, a blood vessel area and a blood flow amount change of an experiment rat. As a result seen in FIG. 2, the blood flow rate, the blood vessel diameter, the blood vessel area and the blood flow amount of the high fat diet control (-) were significantly reduced as compared to the normal control; however the control to which the high fat diet was fed, but the garlic fermented liquid was administrated, showed a similar blood flow rate and blood vessel change with the normal control even through it was subjected to the high fat diet. In particular, the blood flow rate and the diameter of the blood vessel were almost same as the normal control, which means that the garlic fermented liquid is effect on the improvement of the blood circulation.

Figure 3:
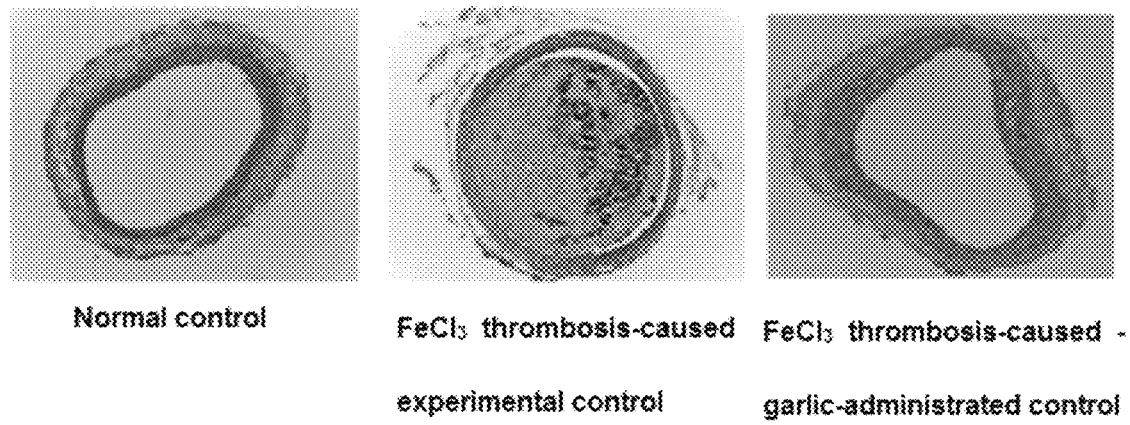
FIG. 3 is a photo showing a blood vessel cut-piece comparison of an experiment rat so as to show a thrombosis creation reduction and a collagenous fiber damage inhibition effect in a blood vessel of a garlic fermented composition according to the present invention.

1-2. Thrombus Creation Decrease and Collagenous Fiber Damage Inhibition Effect in Blood Vessel FIG. 3 is a blood vessel tissue cut-piece comparison photo of an experiment rat. As seen in FIG. 3, the blood vessels were blocked by the thrombosis in the thrombosis-caused experimental control; however the thrombosis of the experiment control to which the garlic fermented liquid was administrated, was all removed like in the normal control. It was confirmed that the garlic fermented liquid removed the thrombosis and completely inhibited the creation thereof.

Moreover, it was possible to confirm that in the thrombosis-caused experimental control, the collagenous fiber of the blood vessel was destroyed, and the blood vessel wall was thinned; however in the experiment control to which the garlic fermented liquid was administrated, it showed that the thickness was similar with the blood vessel wall of the normal control, which meant that the garlic fermented liquid effectively inhibited the damage to the collagenous fiber.

1-3. Obesity Inhibition Effect

Figure 4:
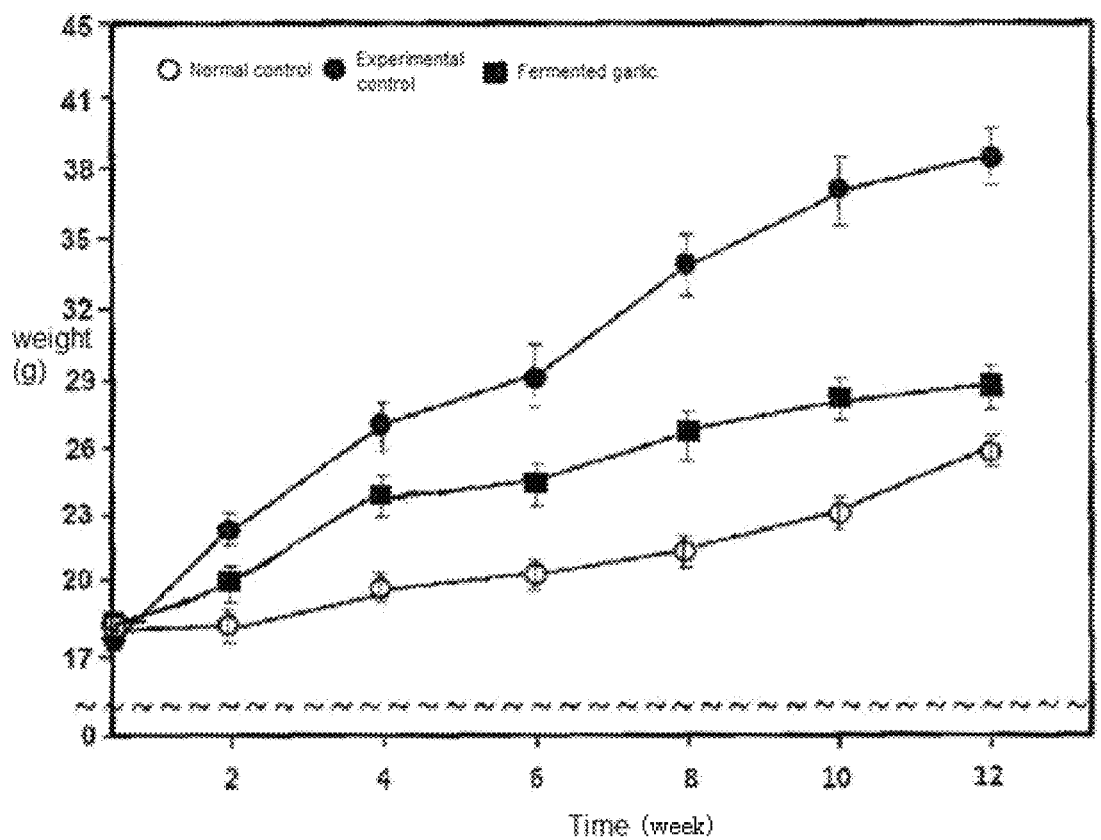
FIG. 4 is a weight change comparison graph of an experiment rat so as to show a weight loss effect of a garlic fermented composition according to the present invention.

FIG. 4 is a weight change comparison graph of an experiment rat. As seen in FIG. 4, the weights of all mice were 18~19 g on the experiment starting date, but as time passed, the weights thereof were increased. After 12 weeks, they were grown to the normal weights of 26.30.9 g, which meant that they grew normally. The weights of the experiment control were greatly increased to 38.51.5 g. The control to which the garlic fermented liquid was administrated, was 27.51.3 g, which meant that the weight was meaningfully decreased as compared to the experimental control, from which it was confirmed that the garlic fermented liquid had effect on the inhibition of the obesity.

1-4. Body Fat Loss Effect

Figure 5:
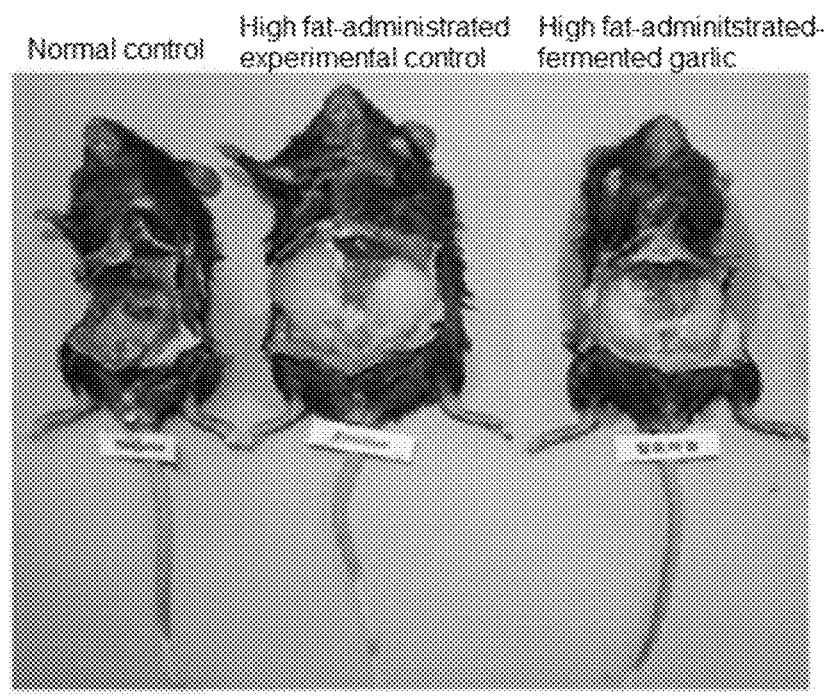
FIG. 5 is a stomach anatomy comparison photo of an experiment rat so as to show a body fat loss effect of a garlic fermented composition according to the present invention.

FIG. 5 is a stomach anatomy comparison photo of an experiment rat. As seen in FIG. 5, it was confirmed that an experimental control to which a high fat was administrated, showed a significantly increased visceral fat as compared to the normal control; however the experiment control to which a high fat and a garlic fermented liquid were administrated, showed a significantly decreased visceral fat as compared to the experimental control to which a high fat was administrated, and showed a significant difference in a body type.

1-5. Blood Pressure Drop Effect

FIG. 5 is a blood pressure comparison graph at a contraction phase of an experiment rat. As seen in FIG. 5, the experimental control to which a high fat was administrated, showed a significant increase in the blood pressure as compared to the normal control; however it was confirmed that the control to which the garlic fermented liquid was administrated, showed a significant drop as compared to the experimental control to which a high fat was administrated.

1-6. Cholesterol Loss Effect

Figure 6:
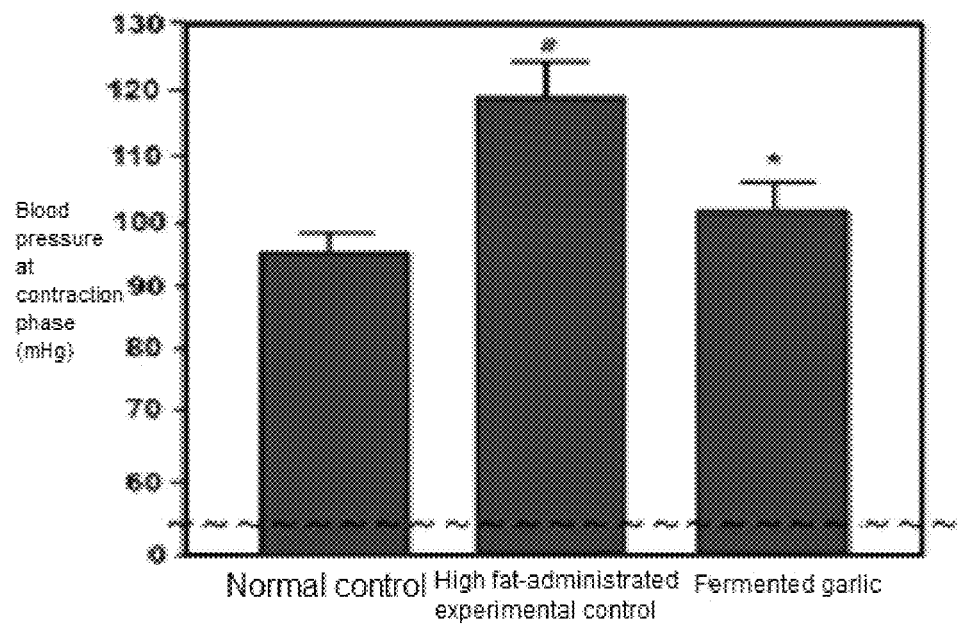
FIG. 6 is a contraction phase blood pressure comparison graph of an experiment rat so as to show a blood pressure decrease effect of a garlic fermented composition according to the present invention.
Figure 8:
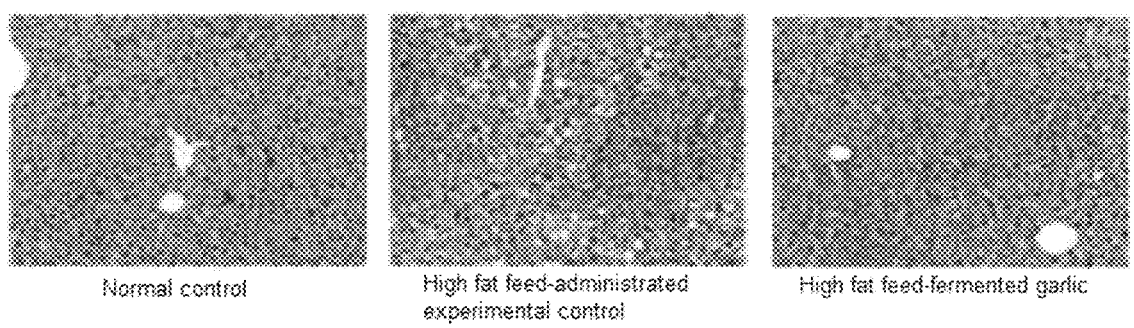
FIG. 8 is a liver tissue cut-piece comparison photo of an experiment photo so as to show a liver cell damage loss effect of a garlic fermented composition according to the present invention.
Figure 9A:
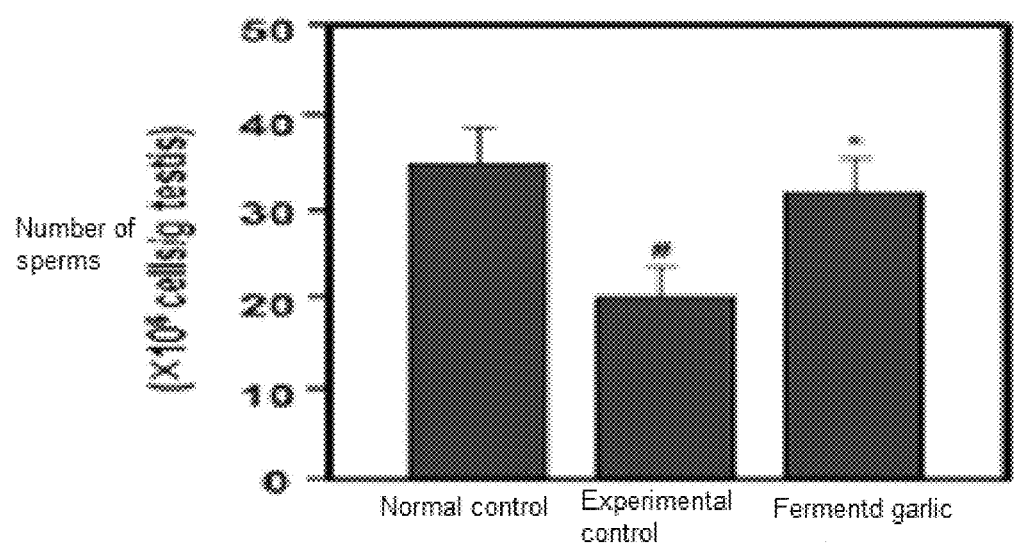
FIG. 9A is a sperm number comparison graph of an experiment rat so as to show a sperm number increase effect of a garlic fermented composition according to the present invention.
Figure 9B:
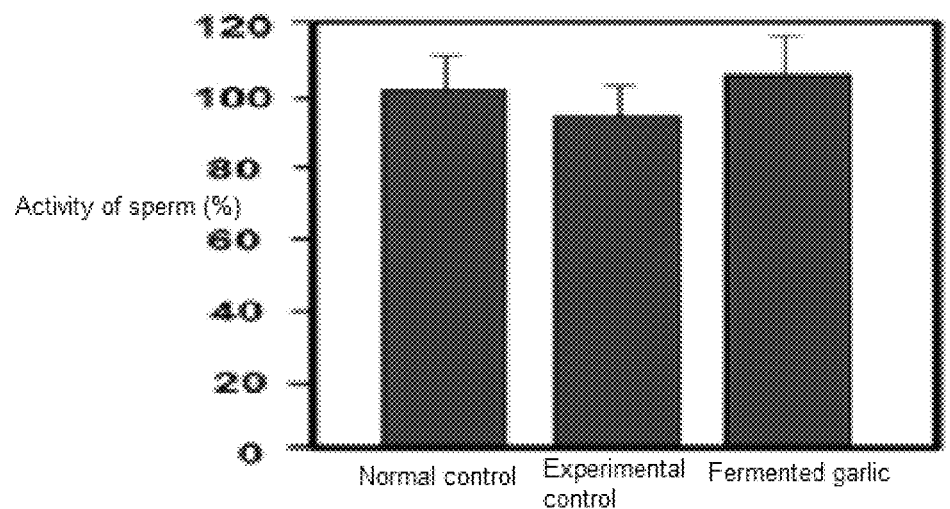
FIG. 9B is a sperm activity comparison graph of an experiment rat so as to show an increased sperm activity effect of a garlic fermented composition according to the present invention.

FIG. 8 is a total blood cholesterol content comparison graph of an experiment rat. As seen in FIG. 6, the total cholesterol content was similar with the normal control and the experimental control to which the garlic fermented liquid was administrated; however the control to which a high fat was administrated, showed a significant increase.

1-7. Liver Cell Damage Decrease Effect

Figure 7:
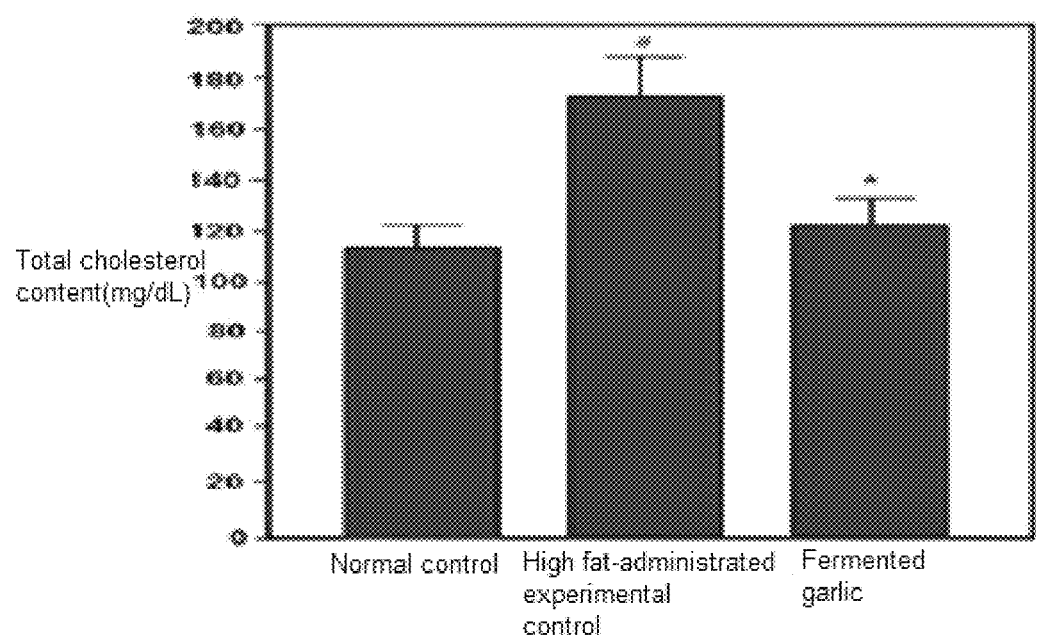
FIG. 7 is a total blood cholesterol content comparison graph of an experiment rat so as to show a blood cholesterol loss effect of a garlic fermented composition according to the present invention.

FIG. 7 is a liver tissue cut-piece comparison photo of an experiment rat. As seen in FIG. 7, the experimental control to which a high fat was administrated, showed a significantly increased fat cell, and a lot of infiltration was observed in a white blood cell, and a liver cell deformation was observed a little; however the control to which a garlic fermented liquid was administrated, showed a similar aspect with the normal control.

1-8. Increases in the Number of Sperms and Activity

FIGS. 8A and 8B are a sperm number and sperm activity comparison graph of an experiment rat. As a seen in FIGS. 8A and 8B, a high fat diet experimental control showed that the number of the sperms was gradually decreased, and in case of the control to which a garlic fermented liquid was administrated, the number of the sperms was increased similar to the normal control. In terms of the activity of the sperms, there was not a meaningful difference, but it was highest in the control to which a garlic fermented liquid was administrated.

1-9. Safety Investigation

As a result of the investigation carried out about a toxicity after the macrophage of an experiment rat was cultivated for 48 hours with a garlic fermented liquid at a concentration of 25~400 μg/ml, there was not a significant difference as compared to the normal control at all the concentrations. Moreover, as a result of the investigation on the weight and internal organs which was carried in such a way that 1 g per 1 kg was repeatedly administrated to 50 experiment rats for 30 days once a day the dosage of which was larger than the amount of one time used for a human body, a special observation was not found, and the color of evacuation didn't show any special symptom. Consequently, it was possible to recognize that there was not any problem with safety of the garlic fermented liquid.

<Experimental Example 2: Animal Experiment> Verification on Brain Disease Improvement Effect The Rose Bengal was administrated to an experiment rat, and the light from a halogen lamp was scanned, and a brain tissue and a blood vessel damage-caused model animal was established, and a garlic fermented liquid was orally administrated for 20 days once a day by 200 mg and 400 mg per 1 kg of the weight, and the effect was verified.

2-1. Evaluation Using MRI

Figure 10A:
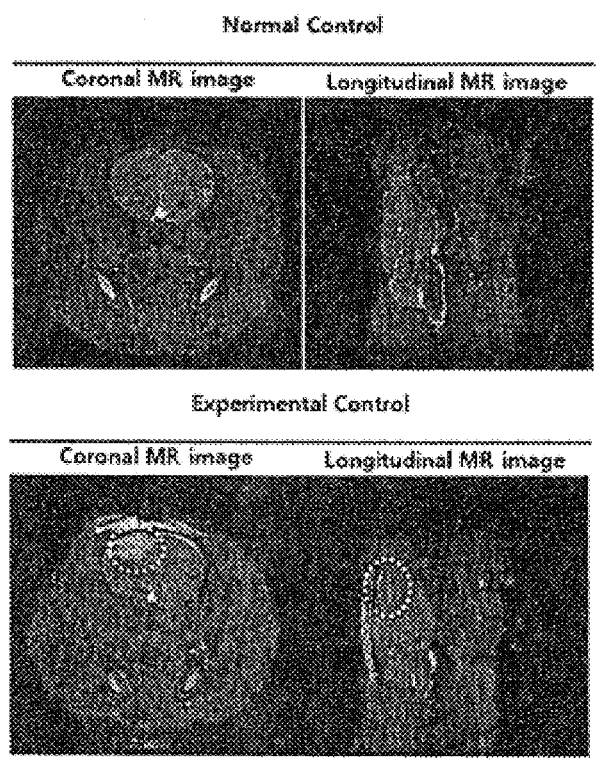
FIG. 10A is a brain tissue MRI comparison photo of a normal control of an experiment rat to which a Rose Bengal was administrated and the light from a halogen lamp was not scanned and an experimental control of an experiment rat to which a Rose Bengal was administrated and the light from a halogen lamp was scanned.

FIG. 10A is a brain tissue magnetic resonance imaging (MRI) between a normal control experiment ray to which a Rose Bengal was administrated, and the light from a halogen lamp was not scanned, and an experiment rat of an experimental control to which a Rose Bengal was administrated, and the light from a halogen lamp was scanned. As seen in FIG. 10A, it was observed that the brain tissue of the normal control was normal, and any damage to the brain blood vessel was not found; however there was a damage to the brain tissue and the blood vessel in the experimental control.

Figure 10B:
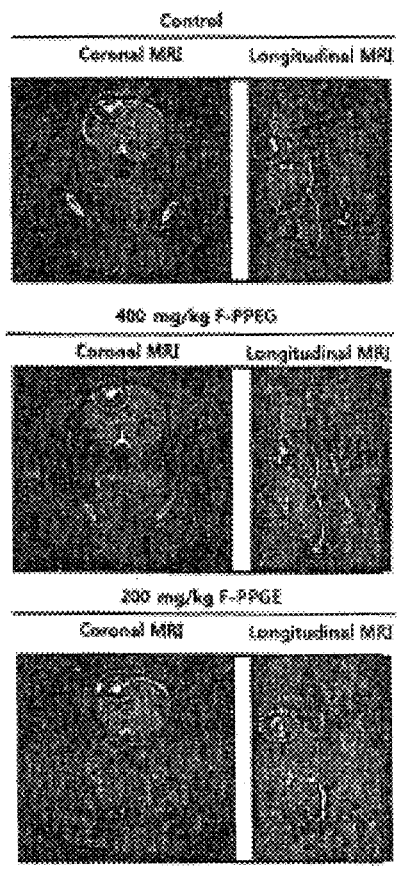
FIG. 10B is a brain tissue MRI comparison photo between an experimental control of an experiment rat to which a Rose Bengal was administrated and the light from a halogen lamp was scanned and an experiment control of an experiment rat to which a Rose Bengal was administrated and the light from a halogen lamp was scanned and a garlic fermented liquid of 200 mg/kg or 400 mg/kg was administrated.

FIG. 10B is a brain tissue MRI comparison photo between an experiment rat of an experimental control to which a Rose Bengal was administrated, and the light from a halogen lamp was scanned, and an experiment rat of an experiment control to which a Rose Bengal was administrated, and the light from a halogen lamp was scanned, and 200 mg/kg or 400 mg/kg of a garlic fermented liquid was administrated. As seen in FIG. 10B, in the experimental control, a brain tissue and a blood vessel were observed clear; however the experimental control to which the garlic fermented liquid was administrated, showed a clear improvement in the brain tissue and the blood vessel. In particular, the control to which 400 mg/kg of a garlic fermented liquid was administrated, showed a clear improvement in a brain tissue and a blood vessel damage as compared to the control to which 200 mg/kg of a garlic fermented liquid was administrated.

2-2. Evaluation Through Brain Tissue Extraction and Tissue Dyeing

Figure 11:
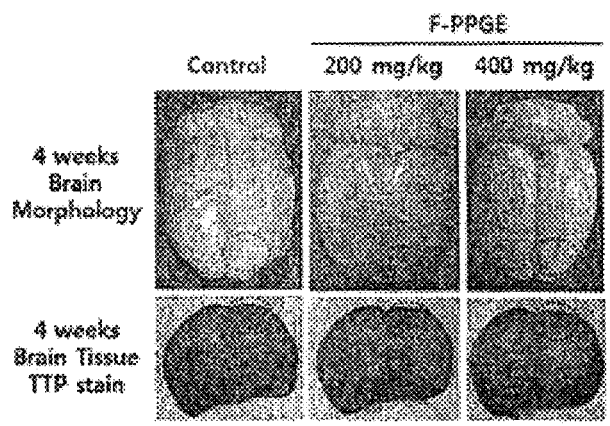
FIG. 11 is a brain tissue comparison photo between an experimental control of an experiment rat to which a Rose Bengal was administrated and the light from a halogen lamp was scanned and an experiment control of an experiment rat to which a Rose Bengal was administrated, and the light of a halogen lamp was scanned, and a garlic fermented liquid of 200 mg/kg or 400 mg/kg was administrated.

FIG. 11 is a comparison photo of a brain tissue extracted from an experiment rat of an experimental control to which a Rose Bengal was administrated, and the light from a halogen lamp was scanned, and an experiment rat of an experiment control to which a Rose Bengal was administrated, and the light from a halogen lamp was scanned, and then 200 mg/kg or 400 mg/kg of a garlic fermented liquid was administrated. As seen in FIG. 11, the experimental control showed a clear brain tissue and blood vessel damage; however the experiment control to which a garlic fermented extract was administrated, showed an improvement in the brain tissue and blood vessel damage. In particular, the control to which 400 mg/kg of a garlic fermented extract was administrated, showed that more improvements in a brain tissue and blood vessel damage as compared to the control to which 200 mg/kg of a garlic fermented extract was administrated.

Figure 12:
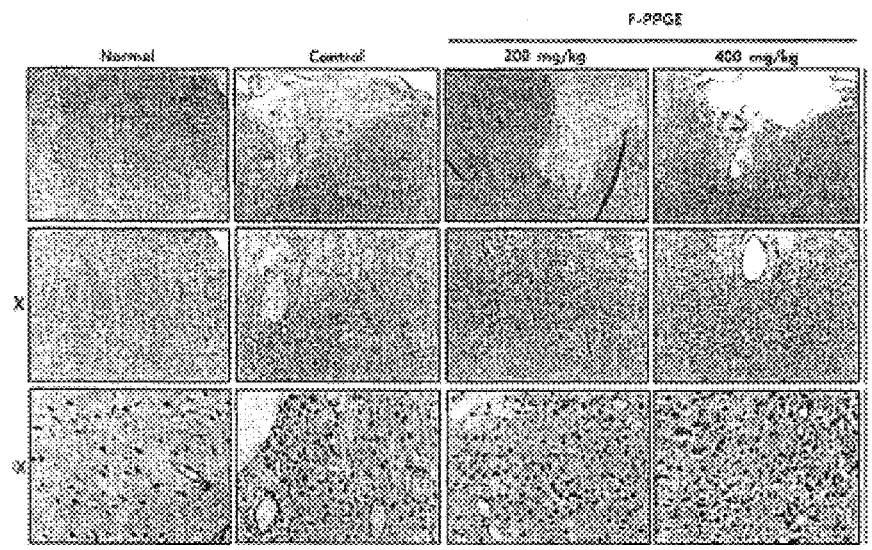
FIG. 12 is a brain tissue cut-piece comparison photo between a normal control of an experiment rat to which a Rose Bengal was administrated and the light from a halogen lamp was not scanned, an experimental control of an experiment rat to which a Rose Bengal was administrated and the light from a halogen lamp was scanned, and an experiment control of an experiment rat to which a Rose Bengal was administrated and the light from a halogen lamp was scanned, and a garlic fermented liquid of 200 mg/kg or 400 mg/kg was administrated.

FIG. 12 is a brain tissue cut-piece comparison photo between an experiment rat of a normal control to which a Rose Bengal was administrated, and the light from a halogen lamp was not scanned, an experiment rat of an experimental control to which a Rose Bengal was administrated, and the light from a halogen lamp was scanned, and an experiment rat of an experiment control to which a Rose Bengal was administrated, and the light of a halogen lamp was scanned, and then 200 mg/kg or 400 mg/kg of a garlic fermented liquid was administrated. As seen in FIG. 12, the experimental control showed that the type of a tissue was significantly damaged as compared to a normal control of experiments, and it was observed that the brain tissue was deformed, and a plurality of inflammatory cells were infiltrated; however the control to which a garlic fermented liquid was administrated, showed a reduced lesion portion, and the number of the inflammatory cells was decreased. In particular, the control to which 400 mg/kg of a garlic fermented extract was administrated, showed a reduced brain tissue and cell damage as compared to the control to which 200 mg/kg of a garlic fermented extract was administrated, and the filtration of an inflammatory immune cells was reduced.

Judging by the aforementioned results, it is confirmed that the administration of the garlic fermented liquid has contributed to an improvement in a brain disease-related tissue or a blood vessel.

<Experiment 3: Animal Experiment> Verification of a Blood Sugar Level Drop Effect The efficacies of the present invention were investigated using "a diabetes mellitus model animal" which caused a type-2 diabetes mellitus in such a way to guide an obesity after a high fat feed had been administrated and to process Streptozotocin (STZ).

3-1. Comparison of Blood Sugar when a Stomach was Empty

Figure 13:
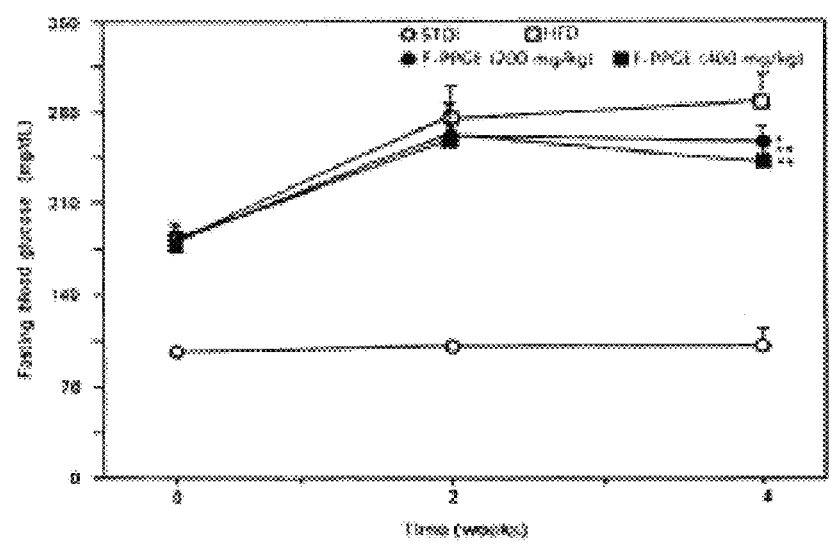
FIG. 13 is a blood sugar comparison graph when the stomach of an experiment rat was empty so as to show a blood sugar drop effect of a garlic fermented composition according to the present invention.

FIG. 13 is a blood sugar comparison graph when the stomach of an experiment rat was empty. In FIG. 13, STD means a normal control to which a standard diet is fed, and HFD means an experimental control to which a high fat diet of which the content of fat accounts for 60%, is fed, and F-PPGE means an experiment control to which a high fat diet and a garlic fermented liquid of 200 mg/kg or 400 mg/kg ware fed.

As seen in FIG. 13, the blood sugar was similar before the start of the experiment of a high fat diet which had caused diabetes mellitus; however the blood sugar was increased as compared to when the experiment had started, in both the experimental control and the experiment control after 2 or 4 weeks. The blood sugar was meaningfully decreased in all the experiment controls as compared to the experimental control after 4 weeks which was the ending date of the experiment. The garlic fermented extract (400 mg/kg) had effect on the decreasing of the blood sugar.

This research result shows that the garlic fermented liquid has effect on the type-2 diabetes mellitus. For this reason, it may be assumed that the present invention may provide a positive influence to the insulin resistance and blood sugar control.

3-2. Comparison of Blood Sugar after the Administration of Glucose 2 weeks after diabetes mellitus was caused by STZ, glucose of 1 g/1 kg was administrated to know a glucose tolerance when the stomach was empty, and a blood was collected from a caudal vein of each experiment rat, and a blood sugar was measured (FIG. 14).

Figure 14:
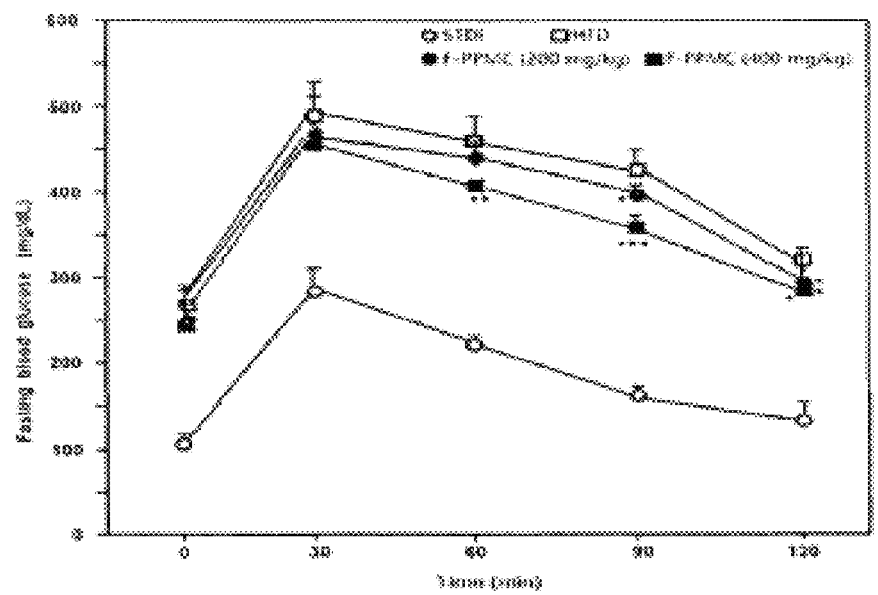
FIG. 14 is a blood sugar comparison graph based on the time lapse after a glucose was administrated to an experiment rat so as to show a blood sugar drop effect of a garlic fermented composition according to the present invention.

As seen in FIG. 14, the blood sugar was peak in the normal control (STD) and the experimental control (HFD) as well as all experiment controls after 30 minutes, and then the blood sugar was gradually decreased thereafter. After 120 minutes, the normal control was completely recovered, so the normal blood sugar was maintained; however in case of the experimental control, the ratio that the blood sugar dropped, was much lower as compared to the normal control.

In case of the control to which a garlic fermented liquid (200 mg/kg or 400 mg/kg) was administrated, the blood sugar was meaningfully dropped 90 or 120 minutes after the administration of glucose.

This research result showed that the garlic fermented liquid had effect on the dropping of the blood sugar 2 weeks after the type-2 diabetes mellitus was caused.

3-3. Comparison of Blood Sugar after the Administration of Insulin 2 weeks after the diabetes mellitus was caused by STZ, insulin was administrated when the stomach was empty, and a blood was collected from a caudal vein of each experiment rat, and a blood sugar was measured (FIG. 15).

Figure 15:
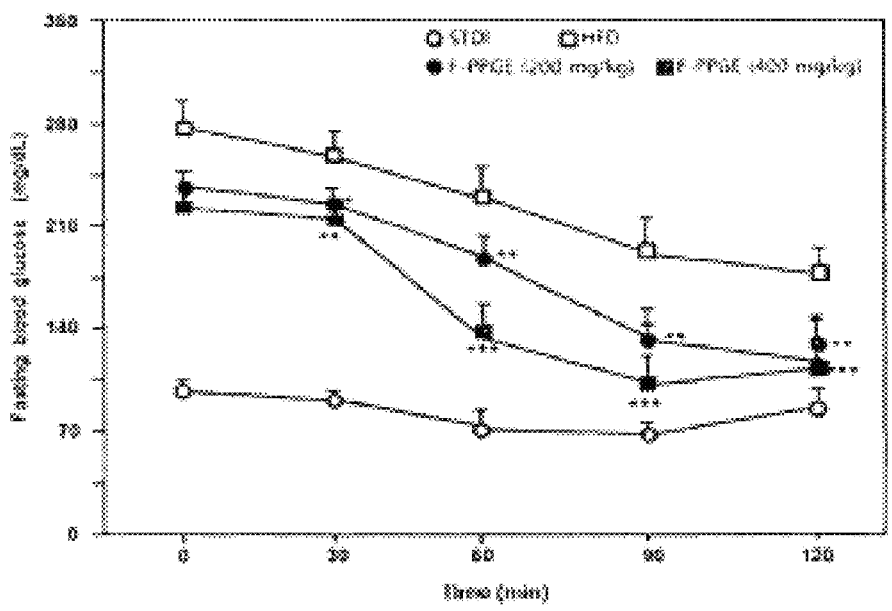
FIG. 15 is a blood sugar comparison graph based on the time lapse after an insulin was administrated to an experiment rat so as to show a blood sugar drop effect of a garlic fermented composition according to the present invention.

As seen in FIG. 15, the blood sugar was increased in the normal control (STD) and the experimental control (HFD) as well as all experiment controls as time passes. After 120 minutes, the normal control was completely recovered, so the normal blood sugar was maintained; however in case of the experimental control, the blood sugar was about 180 mg/dL, which was a high value, after 120 minutes passed.

In case of a garlic fermented liquid (400 mg/kg), it had effect on the dropping of the blood sugar from 30 minutes as compared to the experimental control, and 60 minutes to 120 minutes after the administration of the insulin, all the controls to which a garlic fermented liquid (200 mg/kg or 400 mg/kg) was administrated, had effect on the dropping of the blood sugar as compared to the experimental control (p<0.01, p<0.001).

This research result showed that the garlic fermented liquid had effect on the recovery of the insulin resistance due to an obesity, for which the garlic fermented liquid could be used for the sake of blood sugar control.

3-4. Comparison of Blood Insulin Concentrations

Figure 16:
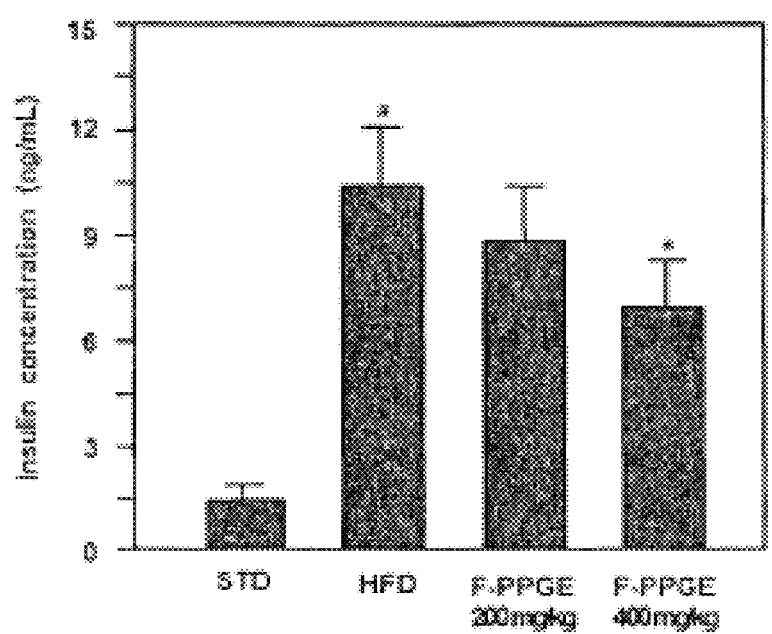
FIG. 16 is a blood insulin concentration comparison graph of an experiment rat so as to show an insulin inhibition effect of a garlic fermented composition according to the present invention.

As a result after the concentration of the blood insulin was checked after the administration of a garlic fermented liquid, as shown in FIG. 16, the concentration of a high fat diet control (HFD) was significantly increased to 10.45 to 1.78 as compared to the normal control (1.05 to 0.56).

The control to which 200 mg/kg of a garlic fermented liquid was administrated and the control to which 400 mg/kg of a garlic fermented liquid was administrated, showed a lowered concentration of the insulin as compared to the experimental control.

This research result showed that the garlic fermented liquid had effect on allowing the blood sugar to increase slowly, not quickly.

Experiment Example 4: A Clinic Experiment 4-1. Blood Pressure Drop Effect

Figure 17B:
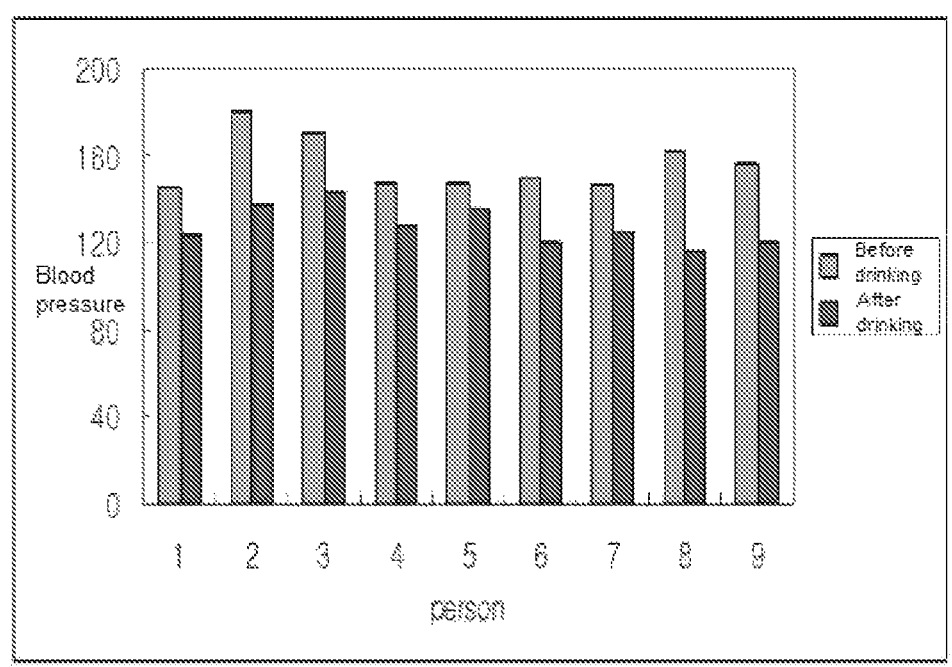
FIG. 17B is a blood pressure comparison graph before and after the drinking of a garlic fermented composition according to the present invention, which was carried out with respect to a hypertension patient.

FIGS. 17A and 17B are a table showing a result of the clinical experiments carried out with respect to each hypertension patient and graphs showing the compared blood pressures before and after the drinking of a garlic fermented liquid. As a result of the clinical experiment, it was confirmed that the blood pressure of the hypertension patient was dropped 20~30% in average 15~30 minutes after the drinking of the garlic fermented liquid, and the state thereof was maintained for over 3 hours.

4-2. Body Temperature Increase Effect

If the body temperature of our body increases 1° C., an obesity prevention, an aging prevention, a dementia prevention, a cancer prevention, a visceral fat loss, etc. can be obtained. If the body temperature decreases, the whole human body activity ability, for example, a metabolism ability, an immunity, an enzyme activity, a digestion ability, a blood circulation, etc. may be lowered. In particular, the immunity level is closely related with the body temperature. According to the known report, whenever the body temperature decreases 1° C., the immunity level may decrease by 30%, and if the body temperature increased 1° C., the immunity level increases 5 to 10 times.

Figure 18:
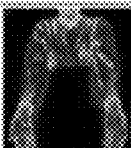
FIG. 18 is an infrared ray body heat diagnosis photo so as to show a body temperature before and after the drinking of a garlic fermented composition according to the present invention.

It is possible to know that a garlic fermented liquid has effect on the increase in a body temperature, which can be seen from an infrared ray diagnosis photo (FIG. 18) showing the body temperatures before and after the drinking of the garlic fermented liquid according to the present invention.

4-3. Blood Vessel Health Enhancement Effects

FIGS. 19A to 19I are photos obtained through a heart pulse wave measurement with respect to a blood vessel health state before and after the drinking of a garlic fermented liquid according to the present invention.

Figure 19A:
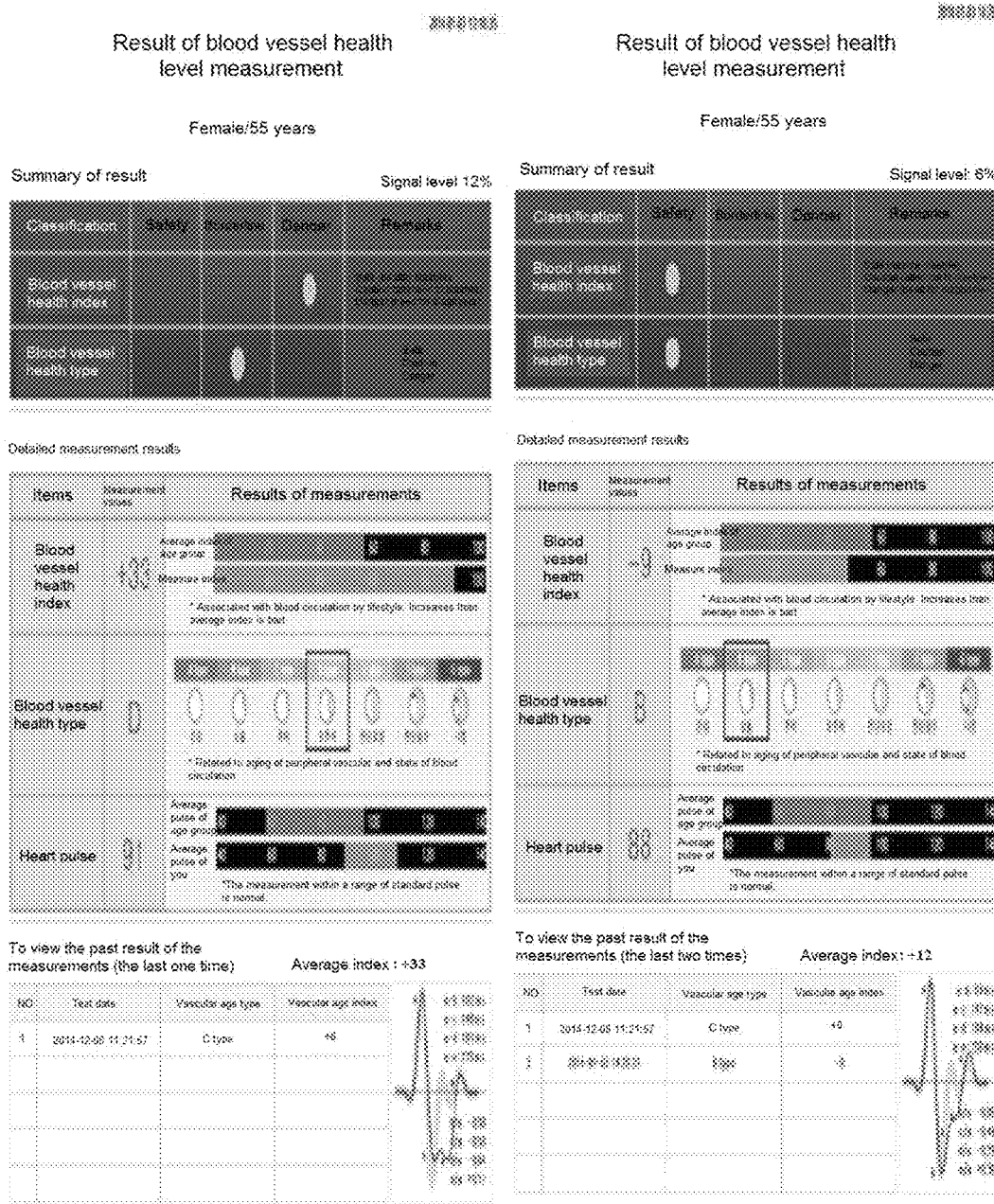
FIGS. 19A to 19I are photos illustrating a heart pulse wave measurement with respect to a blood vessel health level before and after the drinking of a garlic fermented liquid according to the present invention.
Figure 19B:
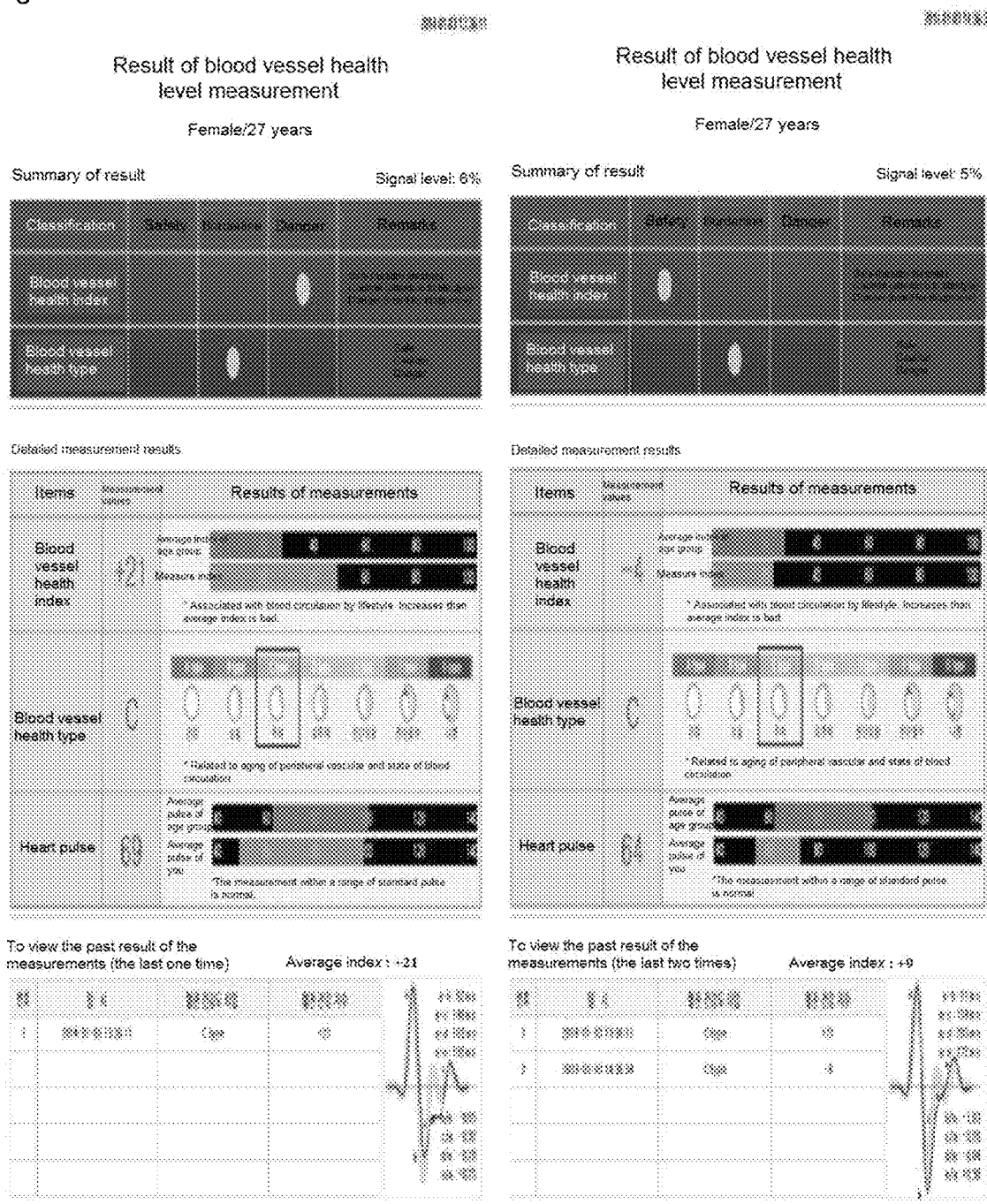
Figure 19C:
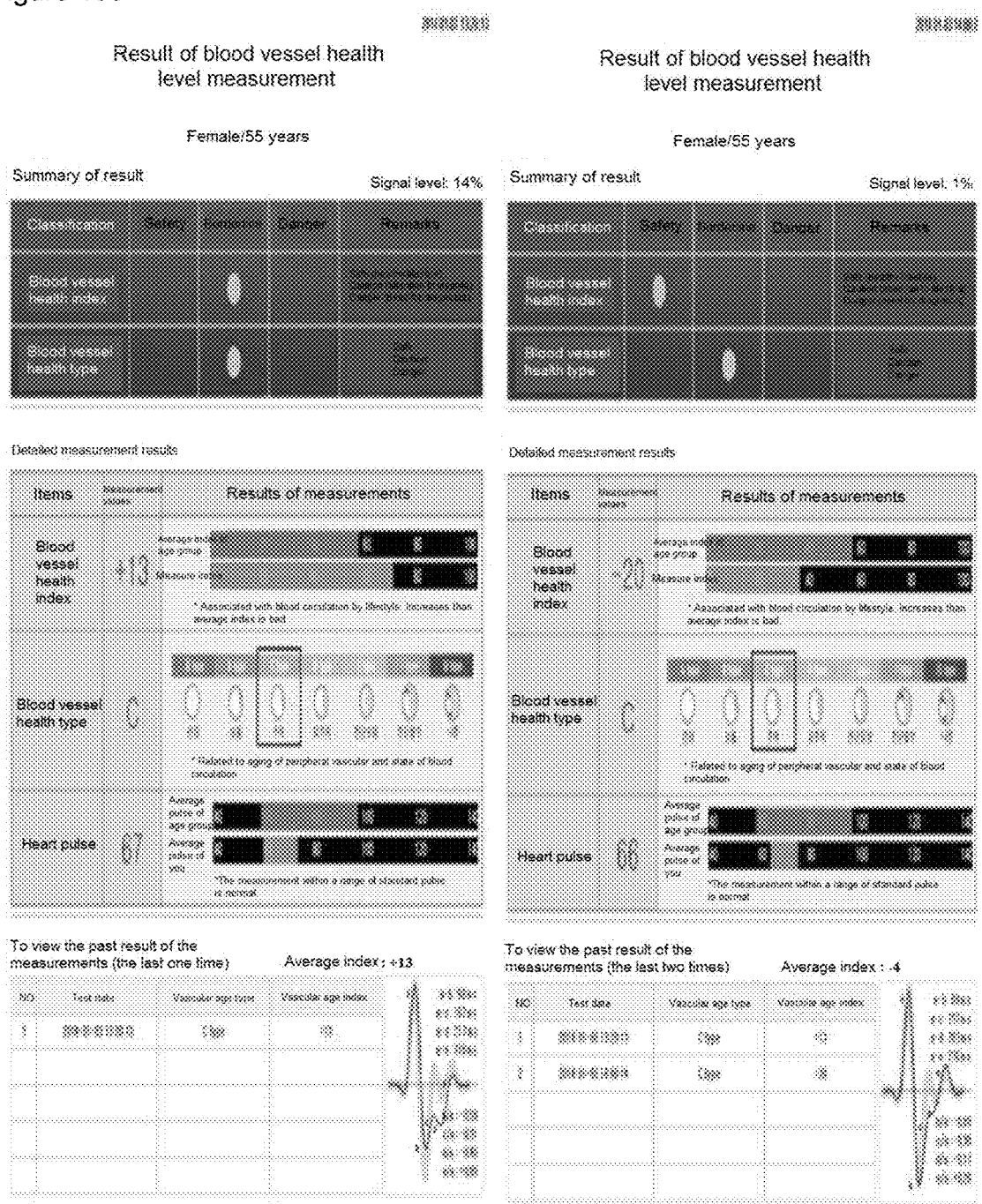
Figure 19D:
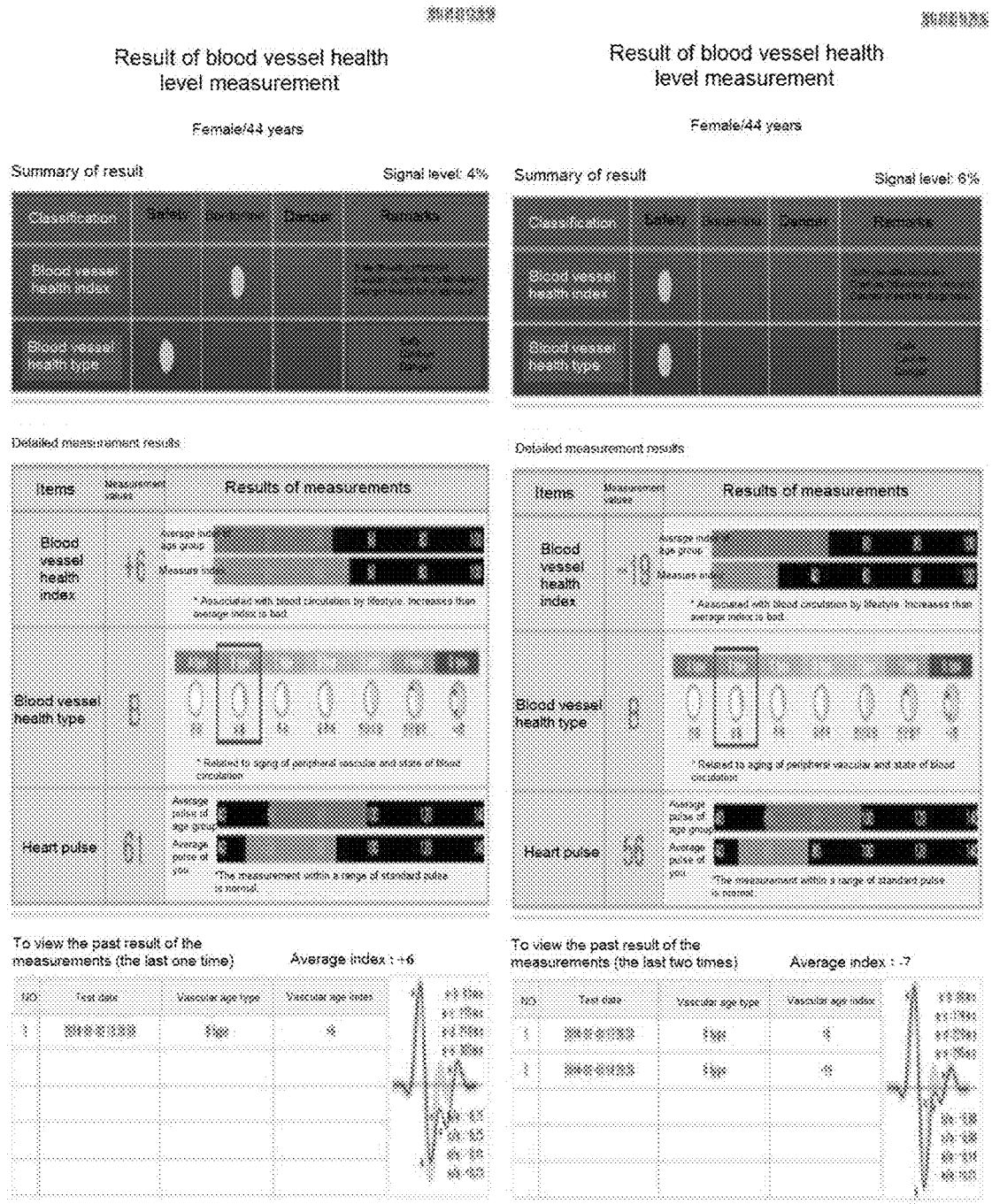
Figure 19E:
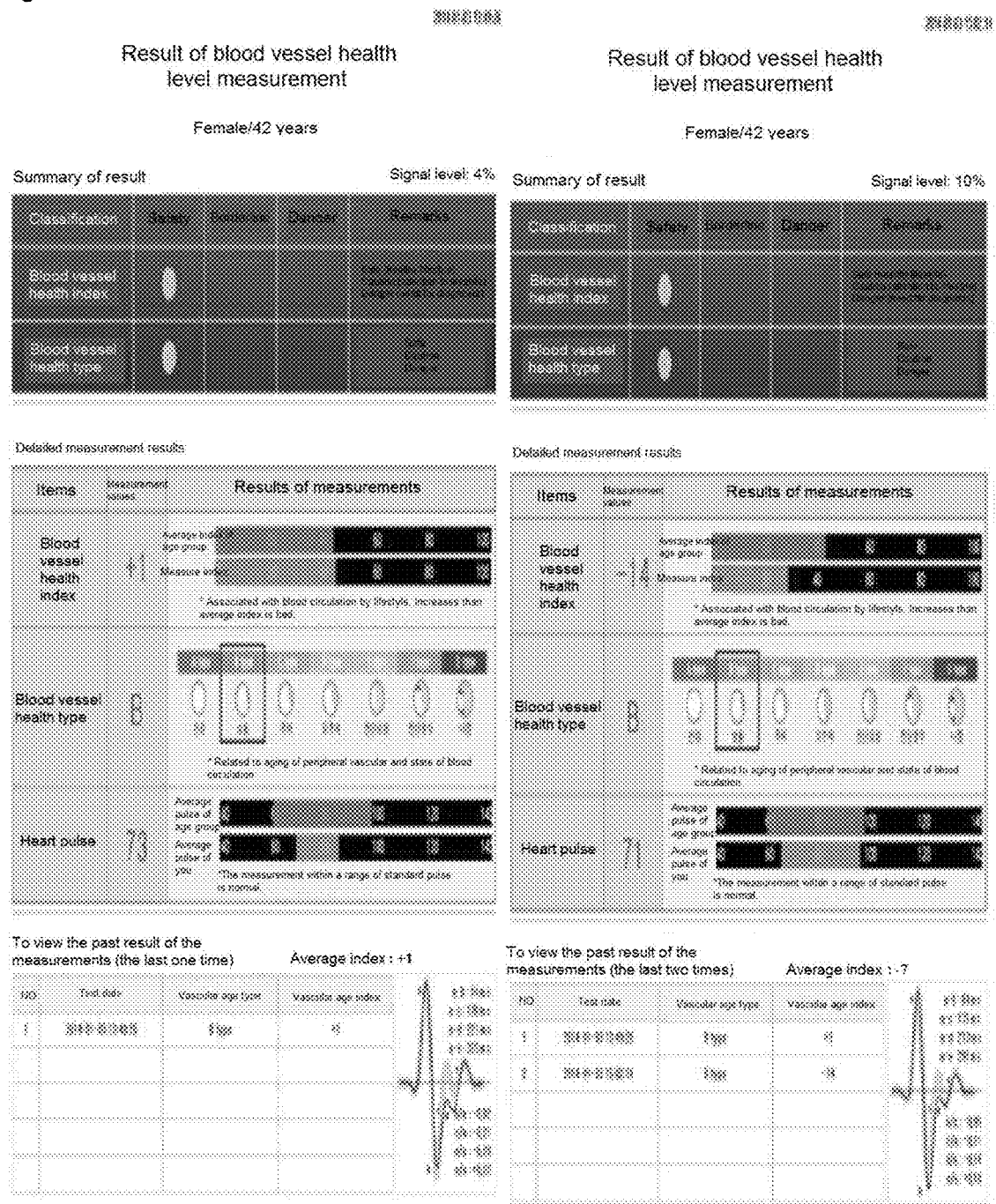
Figure 19F:
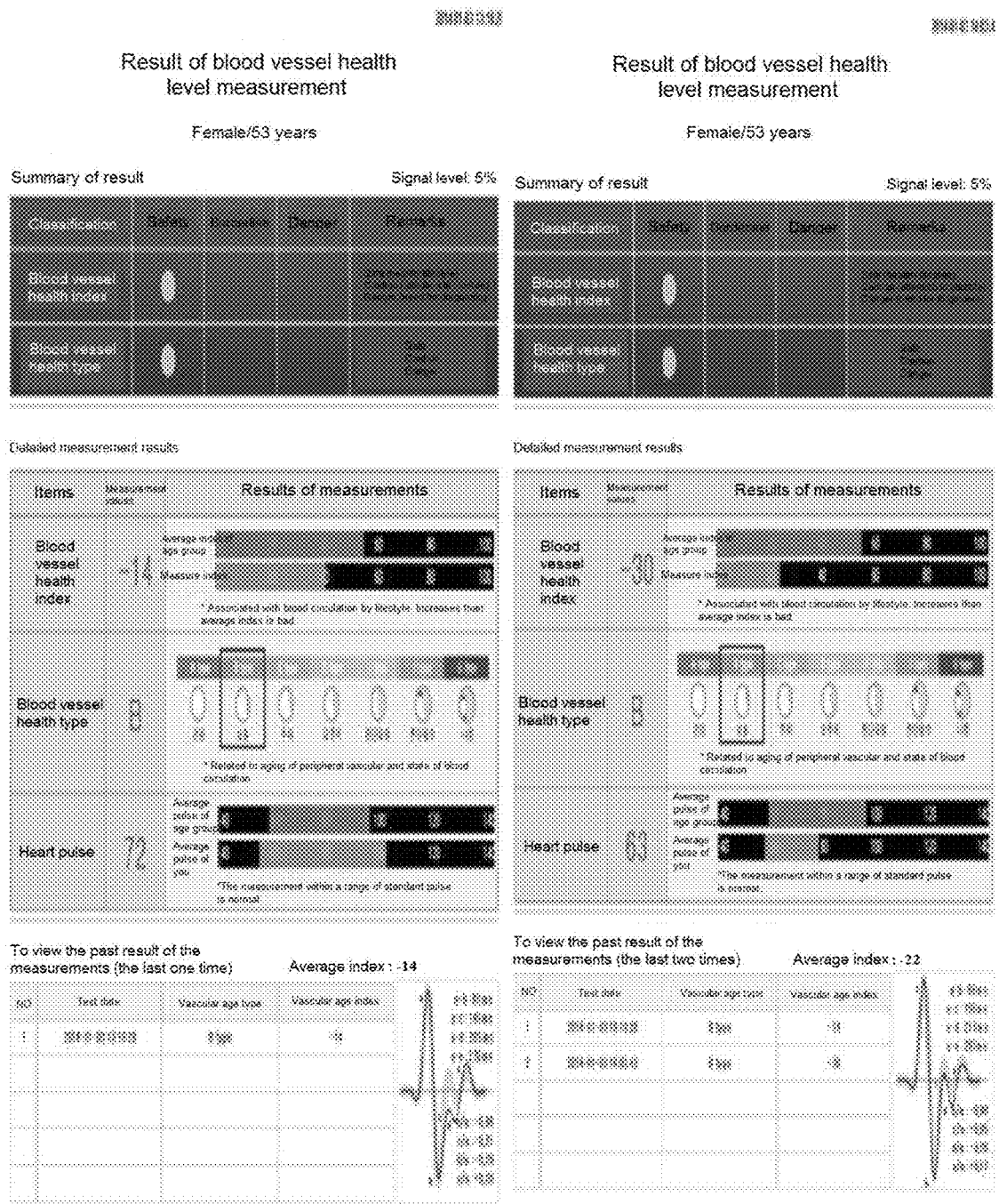
Figure 19G:
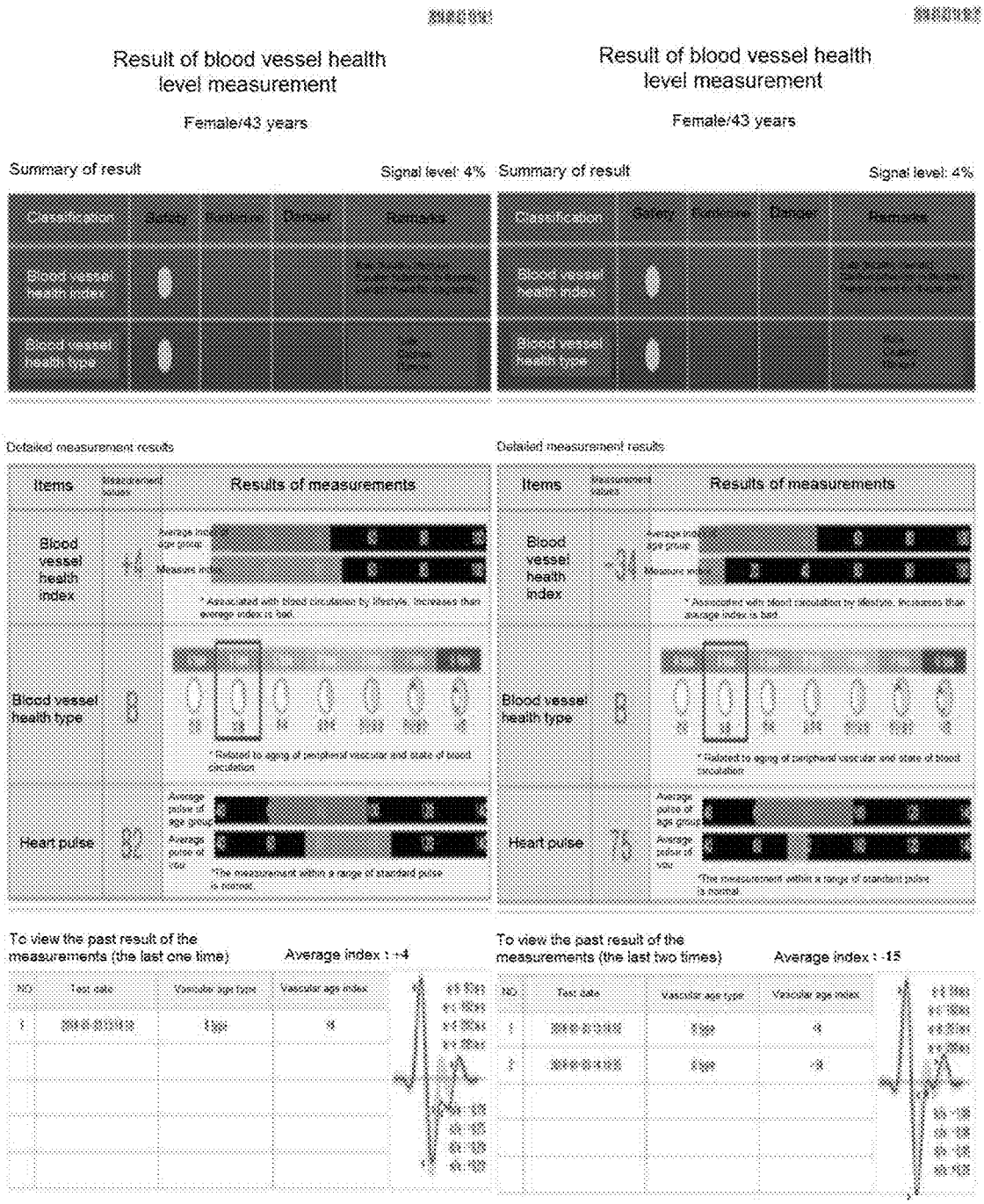
Figure 19H:
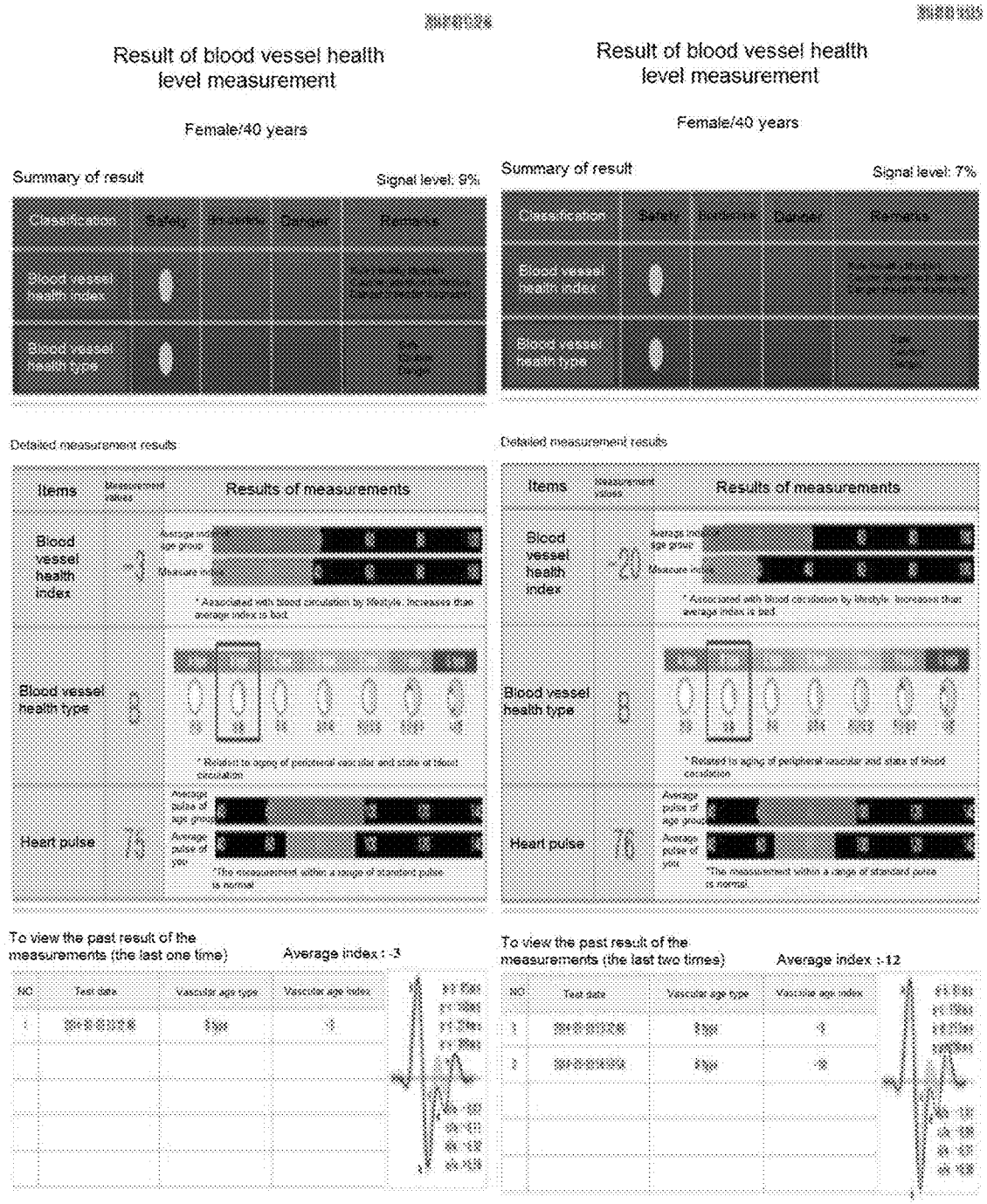
Figure 19I:
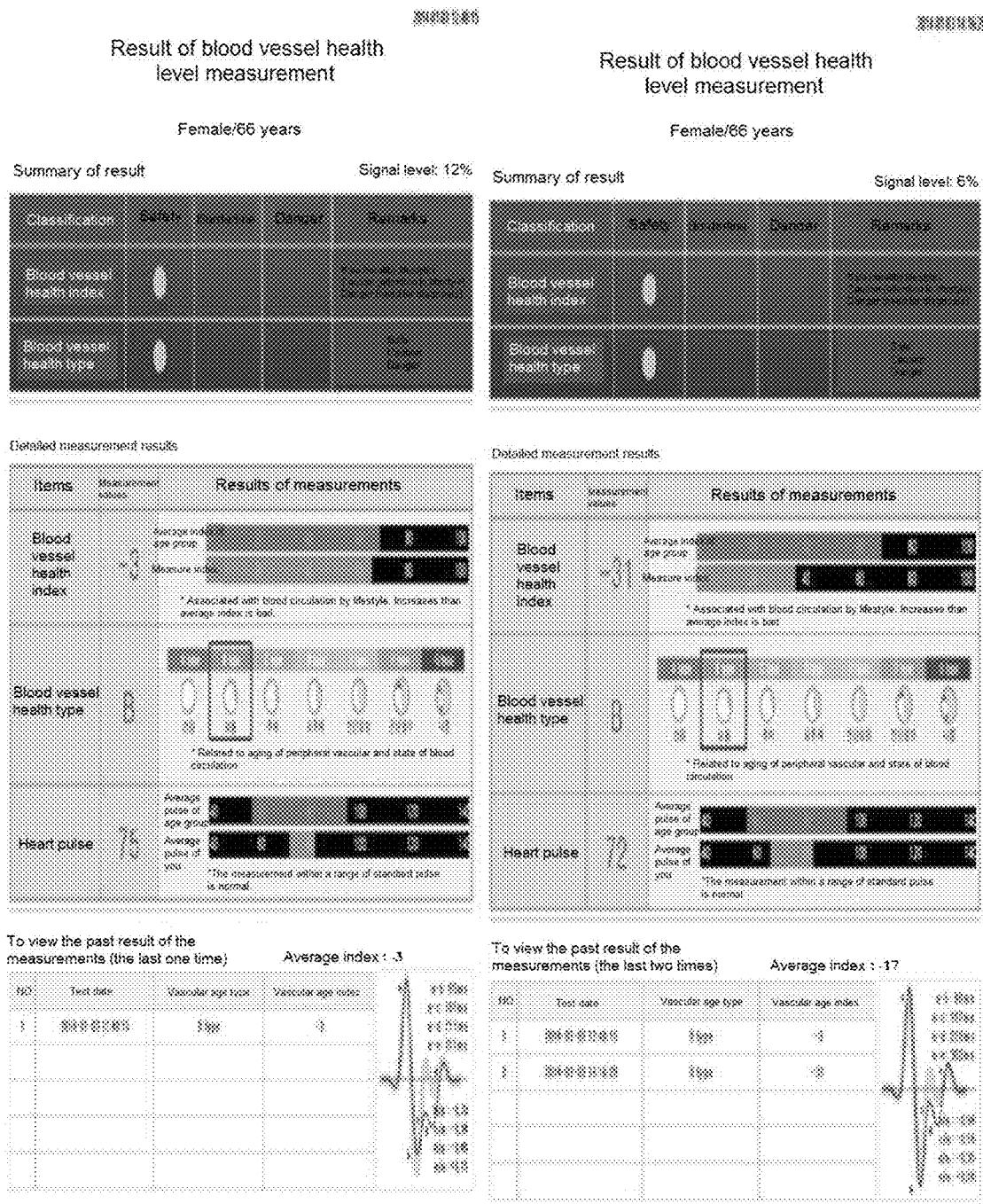

Referring to FIG. 19A, the blood vessel health index was referred to a danger state before the drinking of the garlic fermented liquid, but it became a stable state after the drinking thereof. With regard to the blood vessel health type, it was at a borderline before the drinking; however it recovered to a stable state after the drinking. In case of the blood vessel health index, the measured value was +33 before the drinking, which meant that the age pf the blood vessel was 33 years older than the original age. The measured value was −9 after the drinking, which meant that the age of the blood vessel was 9 years younger than the original age.

It is possible to know that a garlic fermented liquid has effect on the enhancement of the blood vessel health from a result the measurement of the blood vessel health in FIGS. 19A to 19I.

The invention claimed is:

1. A method for preparing a garlic fermented composition, comprising:
    a first fermentation step wherein garlic, water and a fermentation strain are mixed and fermented, thus decomposing and transforming the sugar and protein of the garlic; and
    a second fermentation step wherein a fermentation is carried out in such a way to add a carbon source to a filtrate obtained by separating the fermented mixture into a solid and a liquid, thus eliminating ammonia of the filtrate, and the additionally supplied carbon source is decomposed and transformed,
    wherein in the first fermentation step, a monosaccharaide or a disaccharide and the fermentation strain are added to the water at first to activate the fermentation strain, and then the garlic is added,
    wherein the fermentation strain is a *Bacillus subtilis* subsp. *subtilis* and the first fermentation step is carried out for 3 to 15 days at 20~40° C.,
    wherein in the second fermentation step, the amount of the supply of the carbon source added in the second fermentation step is calculated after the content of the organic substance and ammonia of the filtrate has been quantitatively measured and is referred to the lacking amount of the amount of the organic substance necessary to eliminate the ammonia,
    wherein the content of the organic substance of the filtrate has been quantitatively measured using the CODcr method, and
    wherein the second fermentation step is carried out for 1 to 7 days at 20~40° C. until the sugar level of the filtrate becomes below 0.3 brix.

2. The method of claim 1, wherein the amount of the water is 1-20 times of the garlic with respect to the parts by weight, and the amount of the fermentation strain is 0.011 parts by weight with respect to 100 part by weight of the mixture of the garlic and the water.

3. The method of claim 1, wherein the carbon source is one or more than one mixture selected from a group consisting of a persimmon skin, a kiwi, a pineapple, a pear, a grape, berries, an onion, and a honey.

4. The method of claim 1, wherein the preparation method further includes an ultrafiltration step for eliminating a fermentation strain and a residue of the fermented substance after the second fermentation step.

5. The method of claim 1, wherein the preparing method further includes a disinfection step or a sterilization step after the second fermentation step.

* * * * *